United States Patent [19]
Fujita et al.

[11] Patent Number: 5,976,338
[45] Date of Patent: Nov. 2, 1999

[54] DNA ANALYZER

[75] Inventors: Takeshi Fujita, Hatoyama-machi; Masaharu Kiyama, Higashi-Matsuyama; Shin-ichiro Umemura, Hachioji; Takamichi Muramatsu, Tokorozawa; Yuusuke Miyazaki, Kodama-machi; Masao Kamahori, Kokubunji; Noboru Moriya, Tokorozawa; Shokichi Matsunami, Saitama, all of Japan

[73] Assignees: Hitachi, Ltd.; Hitachi Electronics Engineering Co., Ltd., both of Tokyo, Japan

[21] Appl. No.: 08/837,816

[22] Filed: Apr. 22, 1997

[30] Foreign Application Priority Data

Apr. 24, 1996 [JP] Japan ..................... 8-102566

[51] Int. Cl.⁶ ................................. G01N 27/26
[52] U.S. Cl. ............................ 204/616; 204/621
[58] Field of Search .................... 204/456, 466, 204/467, 607, 616, 617, 618, 621

[56] References Cited

U.S. PATENT DOCUMENTS 3,719,580  3/1973  Roberts et al. ................. 204/619
5,360,523  11/1994 Middendorf et al. ............ 204/457

OTHER PUBLICATIONS

"Alterations of the p53 Gene are Common and Critical Events for the Maintenance of Malignant Phenotypes in Small–Cell Lung Carcinoma", Oncogen(month unknown 1992) 7,451–457. Y. Sameshima, et al.

"Rapid and Sensitive Detection of Point Mutations and DNA Polymorphisms Using the Polymerase Chain Reaction", by M. Orita, et al, Genomics 5, 874–879 (month unknown 1989).

"Heat Transfer" edited by J. P. Holman. pp. 38–39. McGraw Hill 1989 month unknown.

*Primary Examiner*—Robert Warden
*Assistant Examiner*—Alex Noguerola
*Attorney, Agent, or Firm*—Antonelli, Terry, Stout & Kraus, LLP

[57] ABSTRACT

Arranging a pair of temperature control units on both sides of gel 1 and arranging light-transmitting slit 134 on one of the elements, irradiation of an excitation beam over the gel 1 and signal detection are practiced through the slit 134. Introducing dry air onto the slit part, mildew occurrence is prevented on the detecting part. Detecting the power level applied to the gel and calculating the temperature of the temperature control units so that the gel temperature might be a predetermined temperature, on the basis of the detected power level, thereafter carrying out the feedback control of the power level, the gel temperature can be controlled appropriately and strictly during electrophoresis in an automatic fluorescent electrophoresis system, so that high-speed analysis can be done highly reproducibly at a higher voltage applied even by SSCP.

14 Claims, 17 Drawing Sheets

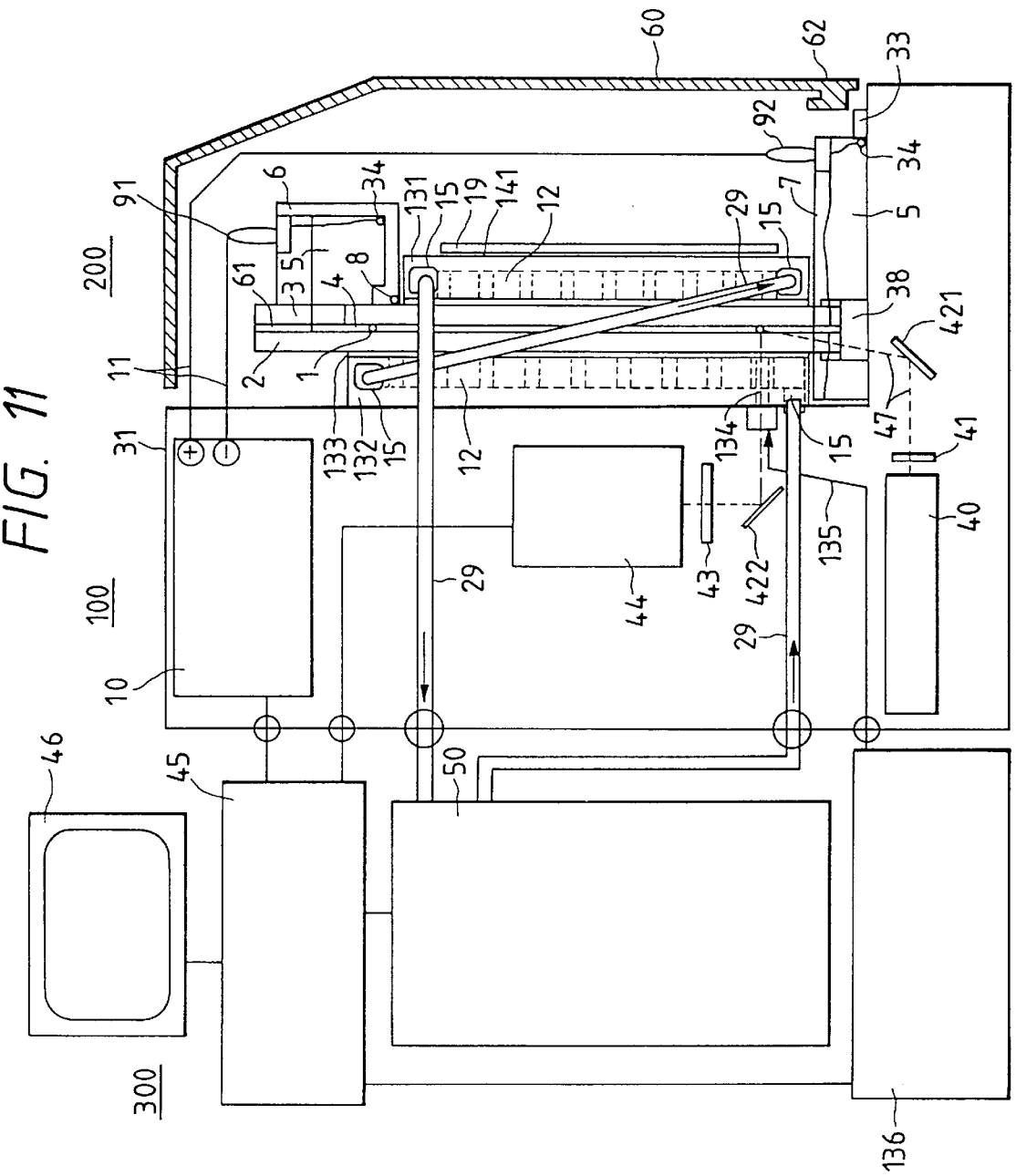

DNA ANALYZER

BACKGROUND OF THE INVENTION

The present invention relates to a gel electrophoresis system for separating and analyzing a biological sample.

Electrophoresis is a method for separating samples, by utilizing the difference in the mobility of the samples in a separation medium, depending on the nucleotide sequence or nucleotide length of a nucleic acid sample or the charge or molecular weight of a biological protein sample. The method is useful as a separation technique in the field of biochemistry. Among them, some of nucleic acid separation is for the purpose of electrophoresis for DNA sequencing or for the purpose of identification of an amplified product after PCR reaction. In this case, the electrophoresis frequently uses slab gel. Essentially, the system of slab gel electrophoresis comprises a gel for separating a sample, glass plates for supporting the gel from both sides thereof, and a pair of electrodes and a power source for applying an electric field through a buffer solution to the gel.

So as to carry out electrophoretic analysis with high resolution at high reproducibility, electrophoretic conditions such as applied voltage and gel composition should be maintained constant, but the gel temperature during electrophoresis is one of difficult-to-control conditions with serious effects on sample separation. The temperature control then has two significant meanings; the gel temperature should be retained uniformly and the gel should be retained at an appropriate temperature.

As to the former one, firstly, non-uniform temperature distribution readily develops in the gel, and therefore, a phenomenon has been remarked problematically such that even the same sample shows a different profile of mobility in some case. The phenomenon is generally called as "smiling", and this problem of non-uniform temperature distribution in the gel occurs because the Joule's heat generated via the passing of elecric current in the gel is not uniformly radiated. It is generally supposed that the reason why the temperature then affects the sample mobility resides in that the viscosity of the buffer solution in the gel varies depending on the temperature.

The latter necessity to control the gel temperature at an appropriate temperature is significant when the electrophoretic temperature for optimum separation varies depending on the sample or the separation method. For example, electrophoresis should be carried out satisfactorily at a temperature of 45 to 55° C. for DNA sequencing; for the SSCP method described in Genomics, Vol. 5, pp. 874–879, 1989, alternatively, the temperature should be retained generally at a predetermined temperature from 4 to 40° C.

Because the SSCP method is a separation method based on the phenomenon that a single-stranded DNA forms a conformation depending on the nucleotide sequence and the mobility during electrophoresis varies depending on the resulting conformation, the method requires that the hydrogen bonding between the nucleotides to maintain the conformation functions in a stable manner. On the contrary, separation methods without utilizing such conformation require a temperature at which not any such conformation is formed.

The SSCP method will now be described in detail below. The optimum temperature for good separation varies depending on the nucleotide length and nucleotide sequence of a sample to be separated, and therefore, the temperature for electrophoresis largely influences the separation outcome. Hence, it is very important to control appropriately and strictly the temperature during electrophoresis.

Another reason requiring the temperature control lies in the demand toward high-speed separation. Following the recent technological progress, the increase of the number of genes to be analyzed demands to shorten the analysis time, which is very readily attained by the high applied voltage for electrophoresis. However, such high-voltage application increases the generation of Joule's heat, thereby raising the gel temperature, which means that more efficient cooling and more precise temperature control will be inevitable than has been attained conventionally.

As has been described above, temperature control of the gel during electrophoresis is a very significant issue from the respect of the demands toward separation at high resolution and high speed. So as to overcome the problem, a means of cooling a slab gel during electrophoresis should be arranged additionally on the essential structure of the system. As disclosed in Japanese Patent Laid-open Nos. Sho 57-163861 and 61-57848, conventionally, a number of methods by means of thermostat plate have been invented.

SUMMARY OF THE INVENTION

The problems described above are to be solved by developing an electrophoresis system, wherein a means for highly efficient heat exchange is arranged on each of the external faces of the plates supporting the gel. In accordance with the present invention, the problems can be overcome by arranging a jacket with a channel on each of the individual external faces of a pair of plates supporting a gel, arranging a liquid coolant circulating unit to follow coolant in the channel, and arranging a temperature control unit for controlling the temperature of the coolant flowing thereby procuring the following functions.

Further to overcome the problems, the present inventors have selected a structure such that a beam-transmitting slit is arranged on at least one of a pair of temperature control units arranged on both sides of a gel, and through the slit, at least one of the irradiation of excitation beam over the gel and the detection of the signal light from the gel can be carried out.

BRIEF DESCRIPTION OF THE DRAWINGS

FIG. 11 depicts a schematic view of automatic fluorescent electrophoresis system;

DESCRIPTION OF THE PREFERRED EMBODIMENTS

Embodiment I

FIG. 10 is a view schematically depicting the flow of Joule's heat generated during electrophoresis, wherein a method via forced liquied convection is described as a means for temperature control. FIG. 10 (A) shows temperature control means arranged on the individual external faces of the plates holding the gel between the plates themselves, encompassing the temperature control method of the present invention. Alternatively, FIG. 10 (B) shows a temperature control means arranged on a single plate, which corresponds to a method by means of a thermostat plate described in Japanese Patent Laid-open No. Sho 57-163861. Herein, heat generated in the gel flowing into only the coolant is modeled. On comparison of FIG. 10 (A) with FIG. 10 (B), the heat flow in accordance with the present invention is described below.

In the individual methods for temperature control, heat flow is discussed, provided that the thickness, composition, and size of a gel, the thickness and material of a plate, and the like are under the same conditions. The gel thickness is defined as L1; the plate thickness is defined as L2; the heat conductivity of the gel is defined as $\lambda 1$; that of the plate is defined as $\lambda 2$; and that of the coolant is defined as $\lambda 3$. The Joule's heat "G" generated in the gel during electrophoresis is represented by the product of voltage "e" and current "i".

Firstly, the temperature distribution in the gel is analyzed. The heat flow inside the plate as an heat source is described in "Heat Transfer", J. P. Holman, eds., McGraw-Hill Book Company, pp.38–39. The model works also for the temperature distribution in the gel. If Joule's heat "G" is represented as heat generation per unit volume "Q", the "Q" is represented by formula 1, given surface area "A" and thickness "L1" to determine the gel volume.

$$Q = \frac{G}{AL_1} \qquad \text{Formula 1}$$

Figure 10A:
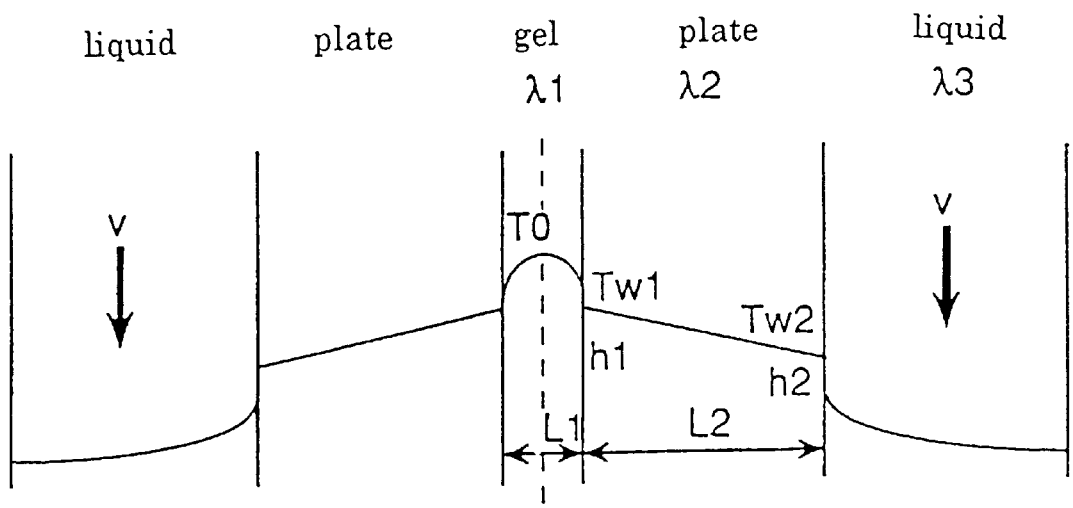
FIG. 10 depicts a view of Joule's heat transfer model during electrophoresis.
Figure 10B:
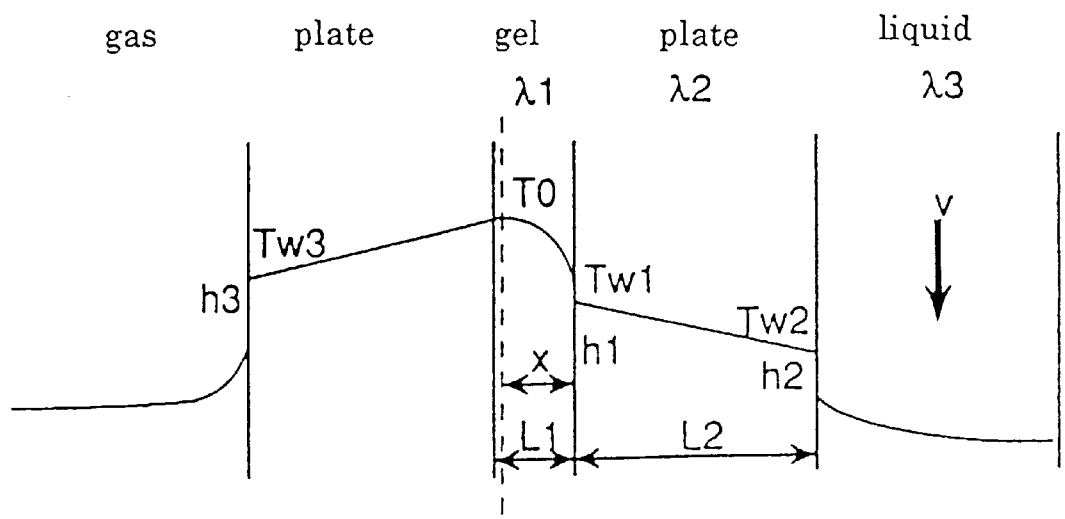

Using the heat generation per unit volume "Q", the highest temperature point in the gel thickness direction and the temperature "T0" at that point should be determined. In FIG. 10(A), the point at T0 is the center of the heat source (gel), so the heat flow can be analyzed on the dotted line functioning as a center line. Thus, only one side from the dotted line may satisfactorily be analyzed, so the whole system may be assumed satisfactorily as a system where the heat generation per unit volume "Q" is transferred and radiated from the center of the heat source (gel) of a thickness of "L1", through the plate, into a coolant at velocity "v". Thus, formula 2 is given.

$$T_0 - T_{w1} = \frac{Q\left(\frac{1}{2}L_1\right)^2}{2\lambda_1} = \frac{QL_1^2}{8\lambda_1} \qquad \text{Formula 2}$$

Herein, "Tw1" means the temperature of a plate face in contact to the gel; "Tw2" means the temperature of a plate face in contact to the coolant.

In FIG. 10 (B), alternatively, it is configured that one of the plates faces air as a gas, while the other plate faces the coolant flow. The extent of heat flow from a heated plate to the coolant flowing in the external face is represented by heat conductivity "h" (W/m$^2$.K). If comparison is made between gas and coolant as the substances flowing in the external faces, coolant has a larger heat conductivity by two orders. Thus, the heat conduction level onto the single side facing air is far smaller than the level onto the other side facing the coolant, so the point at "T0" is not the center of the gel but lies in a point sifted toward the plate facing air. Provided that the distance between the point at "T0" and the side facing coolant is represented as "x", "x" is approximately assumed to be L1. Thus, the temperature difference between T0 and Tw1 is in proportion to the square of the distance "x". Accordingly, the difference is assumed to be 4-fold at maximum that of the value calculated by formula 2.

Then, the Joule's heat passing through the plates is analyzed. The Joule's heat passing through the plates should be designated as heat generation per unit volume, namely heat flux. The heat flux "q" is represented by the following formula.

$$q = \frac{G}{A} \qquad \text{Formula 3}$$

In FIG. 10 (A), heat flux "q/2" passes through a plate of heat conductivity "l2" and thickness "L2", to conduct the heat to a coolant at flow rate "v" on the plate surface. Then, the temperature difference "Tw1–Tw2" on both the sides of the plate is represented by the following Formula.

$$T_{w1} - T_{w2} = \frac{q}{2}\left(\frac{1}{h_1} + \frac{L_2}{\lambda 2} + \frac{1}{h_2}\right) \qquad \text{Formula 4}$$

Herein, "h1" represents heat conductivity between the gel and the plate. "h2" represents the heat conductivity between the plate and the flowing coolant. "h1" will be infinite under the provision of no conductivity loss. Alternatively, "h2" is of a value variable, depending on the coolant properties and flow rate, so the value should be determined under various conditions.

In FIG. 10 (B), alternatively, heat flux 2-fold at maximum the flux in FIG. 10 (A) flows onto the plate on a single side, and therefore, the value of "Tw1–Tw2" is assumed to be 2-fold that of double-sided temperature control.

The heat conductivity "h2" is determined by Reynolds number "Re" representing the flow characteristics of a substance on the basis of fluid flow rate and viscosity, Nusselt number representing the intensity of heat conduction between the fluid and a plate, and non-dimensional Prandtle number "Pr" serving as a bridge between the flow and heat transfer. By serially determining these non-dimensional numbers, the heat conductivity "h2" can be determined. Firstly, the Reynolds number is represented by the following formula, given the rate "v" of a flowing substance, the dynamic viscosity coefficient "n" thereof and the representative length "Ls" thereof.

$$Re = \frac{vLs}{v} \qquad \text{Formula 5}$$

In the formula 5, "Ls" generally represents tube diameter, but in the case of square tube or semi-circular tube, it is experimentally verified that "Ls" corresponds to a value calculated by dividing the cross sectional area by the length of the wet circumference and multiplying the resulting value by 4. The Re number can be determined from these values. It is determined whether the substance flow is turbulent flow or laminar flow, on the basis of the value of the Re number; generally, the flow is designated as turbulent flow at an Re number above $3.2 \times 10^5$. Because the Pr number is a value determined only by the fluid properties, then, the Mechanical Engineering Handbook (Maruzen), etc. should be referred to. For example, the Pr number of water is 7.11 at 20° C. Then, the Nu number is determined on the basis of the values of the Re number and the Pr number, as represented by the experimental formula described in "Heat Transfer Engineering".

$$Nu = 0.332 \, Pr^{1/3} Re^{1/2} \quad \therefore 0.6 < Pr < 15 \qquad \text{Formula 6}$$

"h2" is determined by the following formula, using the resulting value of the Nu number.

$$h_2 = \frac{Nu\lambda_3}{L_3} \qquad \text{Formula 7}$$

In the reference, approximate "h" values are generally described, so their values are shown in the following table for reference.

TABLE 1

| Flow type | Flow state | Heat conductivity (W/m² · K) |
|---|---|---|
| Free convection | atmospheric plane | 6 |
|  | plane in water | 810 |
| Forced convection | air flow in tube | 47 |
|  | water flow in tube | 5800 |

As shown above, the "h" value increases as the coolant flows in a more enforced fashion, and the coolant is most efficiently a liquid. More specifically, the increase of the flow rate is significant so as to raise the heat conductivity, and for the purpose, the pump flow level should be raised and the tube diameter for water flow should be narrowed, effectively.

When both the fundamental formulas 2 and 3 from double-sided temperature control are to be united into a single formula by using Tw1, the value of T0 can be determined, depending on the temperature Tw2, which is shown in the following formula.

$$T_0 = T_{w2} + \frac{G}{2A}\left(\frac{L_2}{\lambda_2} + \frac{1}{h_2} + \frac{L_1}{4\lambda_1}\right) \qquad \text{Formula 8}$$

By using the formula 8, it can be said that the gel temperature during electrophoresis can be calculated on the basis of the applied voltage and current levels and the temperature of a coolant flowing on the external face of a plate.

The present invention is to provide a double-sided temperature control method by the above means, so the fundamental formulas calculating the temperature difference inside the gel (T0–Tw2) or the temperature difference between the two sides of the gel under double-sided temperature control (Tw1–Tw2), can be used to bring about the following advantages. As shown in the fundamental formulas, the temperature difference inside the gel can be made smaller through the double-sided temperature control than the difference by a method using a thermostat plate as one example of conventional methods. Thus, temperature environment favoring toward uniformity can be procured for sample separation. Because the transfer of the Joule's heat from the gel is doubled to increase the heat exchange efficiency, the difference between the flowing coolant temperature and the gel temperature can be made small, since the temperature difference between the two sides of the plate should be ½-fold that of single-sided temperature control. This indicates that even the increased generation of Joule's heat at a higher voltage applied can be cooled efficiently. Comparing a method by means of a buffer solution as the coolant, the method of the present invention realizes heat exchange without using buffer solutions as the coolant. Therefore, no electric current should necessarily be passed through the coolant.

The system structure and control method specifically representing the present invention will further be described in examples.

Examples

Figure 1:
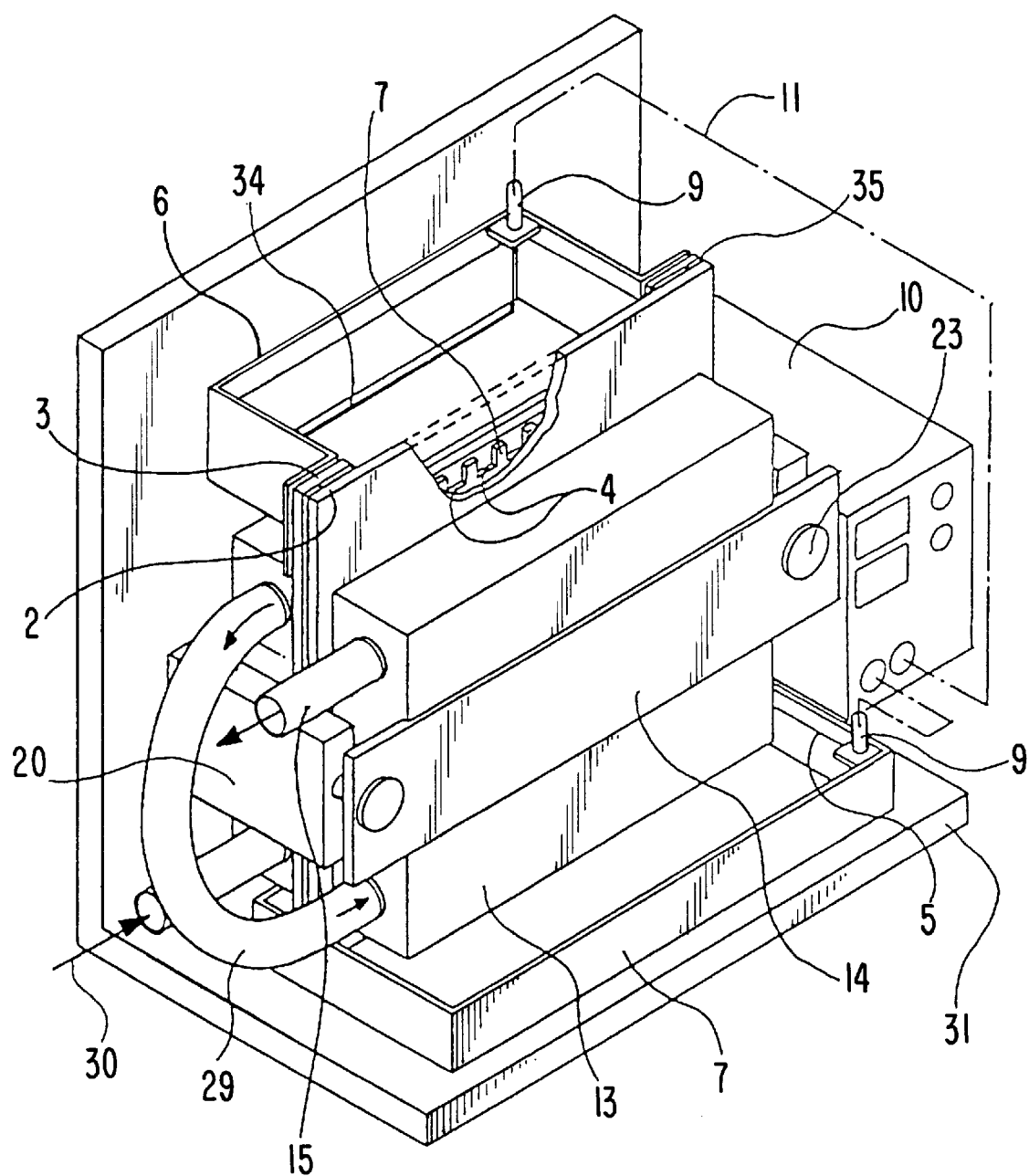
FIG. 1 depicts a view of the slab gel electrophoresis system of the present invention.
Figure 2:
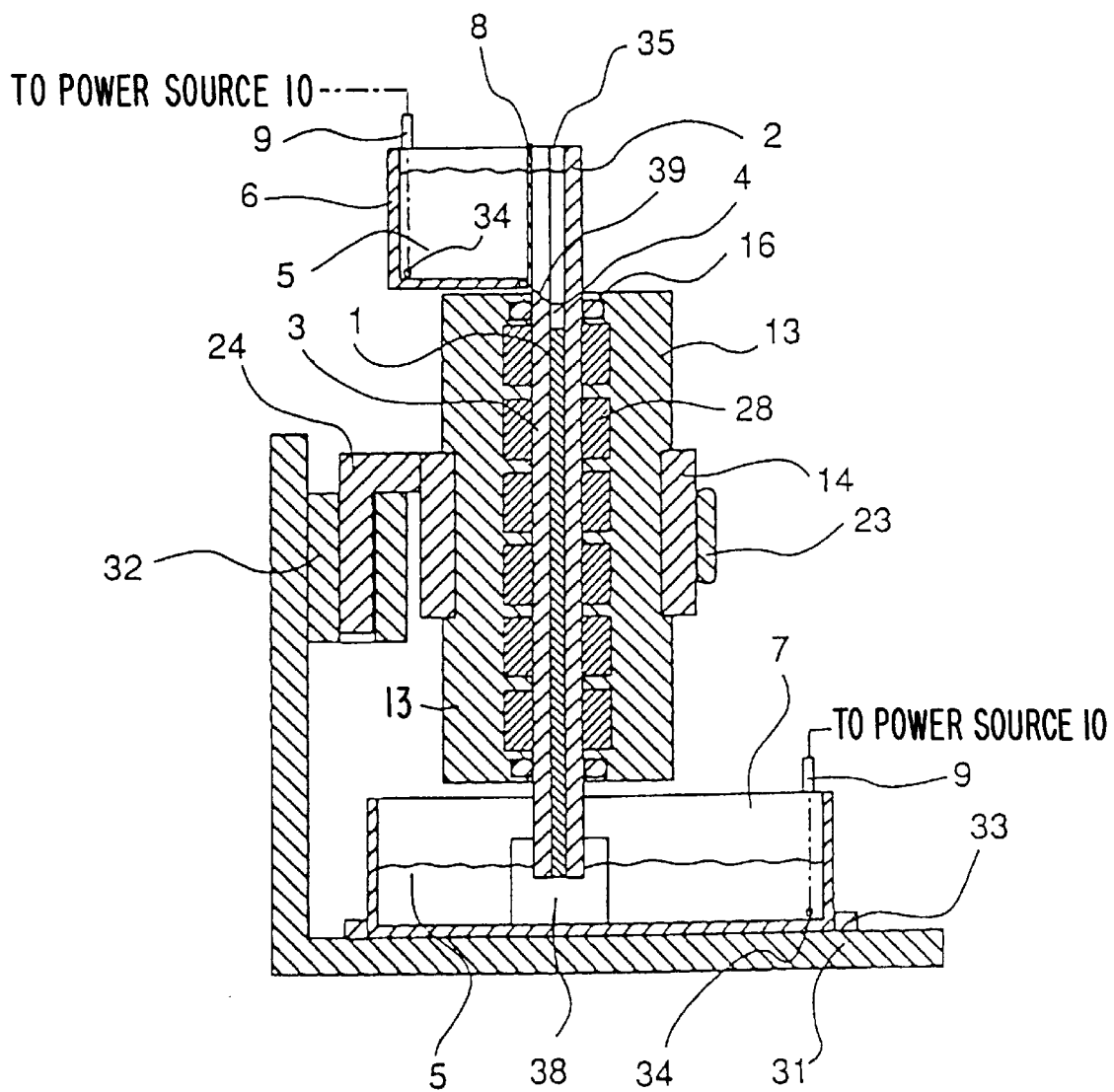
FIG. 2 depicts a cross-sectional view of the electrophoresis system shown in FIG. 1.

FIG. 1 depicts a perspective view of an electrophoresis system using slab gel as one example of the present invention; and FIG. 2 depicts a cross-sectional view of the electrophoresis system. As the gel material, use may be made of general gels such as polyacrylamide and agarose. Additionally, so-called gradient gels with variable gel concentrations or gels with modified levels of denaturing agents, may satisfactorily be used as well.

Firstly, the essential structure for carrying out electrophoresis will be described. In FIG. 1, Gel 1 is placed between glass plate 2 and notched glass plate 3. The method for preparing a gel plate generally comprises pouring a non-polymerized material into the space with spacer 35 interposed between the glass plates 2,3 and inserting a shirk comb (not shown in the figure) for supporting a sample to be separated. In the present invention, the glass plates 2,3 of a 20-cm square were used as standards, and the size of the gel prepared from the plates was approximately 19 cm (width)× 15 cm (length)×0.35 mm (thickness). But these sizes of the glass plates and gel are only illustrated representatively. These sizes should be modified appropriately, depending on the analytical method, the gel material, and the type of a biological sample to be separated. Because the gel size is highly responsible for the generation of Joule's heat as a significant issue of the present invention, these sizes should be determined particularly carefully. More specifically, a longer dimension of the gel along the direction of voltage application increases the resistance value involving the decrease of Joule's heat in generation and also involving the narrowed width. Otherwise, a thinner thickness may decrease the generation of Joule's heat. For selecting the dimension of the gel, the minimum essential length capable of separating a subjective sample should be selected along the longitudinal direction; while the minimum essential width should be selected, depending on the number of samples to be separated simultaneously. Depending on a variety of purposes of analysis, the thickness should be selected, and therefore, the thickness cannot be defined generally. The thickness of for example polyacrylamide gel should be within a practical range of 0.2 to 0.4 mm, while the thickness of agarose gel is within a practical range of 0.4 mm to 1 mm.

The material of the glass plates 1,2 should have properties to confer surface flatness and higher thermal conductivity along with uniform thickness, preferably including quartz glass and soda glass. Taking into account the detection of a sample after electrophoresis, furthermore, a method comprising preliminarily labeling a sample with fluorescence and visually observing the resulting sample while the gel is still interposed between the plates, is often selected for fluorescent detection. Hence, it is required that the plate has good optical transmission properties with no fluorescent substances contained therein, and therefore, quartz glass is preferable. Additionally, the thickness of the glass plates is preferably thin, but because the glass plates function to hold the gel flat, the glass plates never be distorted under the load of itself at a selected thickness.

The mode of electrophoresis will be described in detail. The gel 1 and the glass plates 2,3 thus prepared are arranged (the arranging method will be described hereinafter). If the shirk comb is removed prior to electrophoresis, a plurality of sample grooves 4,4, - - - are prepared along (the track of) the shirk comb, so samples to be separated should be filled in the sample grooves 4, 4, - - - . Thus, a plurality of grooves are prepared on the gel upper end part, so a plurality of biological samples can be placed during electrophoresis to enable their separation under the same conditions. The upper end face and lower end face of the gel 1 are immersed in buffer solution 5, and the buffer solution 5 is reserved in upper buffer solution tank 6 and lower buffer solution tank 7. Notched end face 39 of the notched glass plate 3 is beveled as shown in FIG. 2, which helps top parts of syringes and the like readily inserted into the sample grooves when the samples are to be introduced therein. Furthermore, the upper buffer solution tank 6 is fixed with clip (not shown in the figures) or the like onto the external face of the notched glass plate 3, and a notch of the same shape as the notch of the glass plate is arranged on the upper buffer solution tank 6 and additionally, sealing material 8, preferably silicon sponge, is arranged following the shape of the notch, to compose a structure such that the leakage of the buffer solution 5 never occurs from the upper buffer solution tank 6. Platinum wire 34 is fixed in each of the upper and lower buffer solution tanks, and one end thereof is connected to banana-clip-type joint 9, and the joint 9 is connected to power source cable 11 connected to electrophoretic power source 10.

Figure 3:
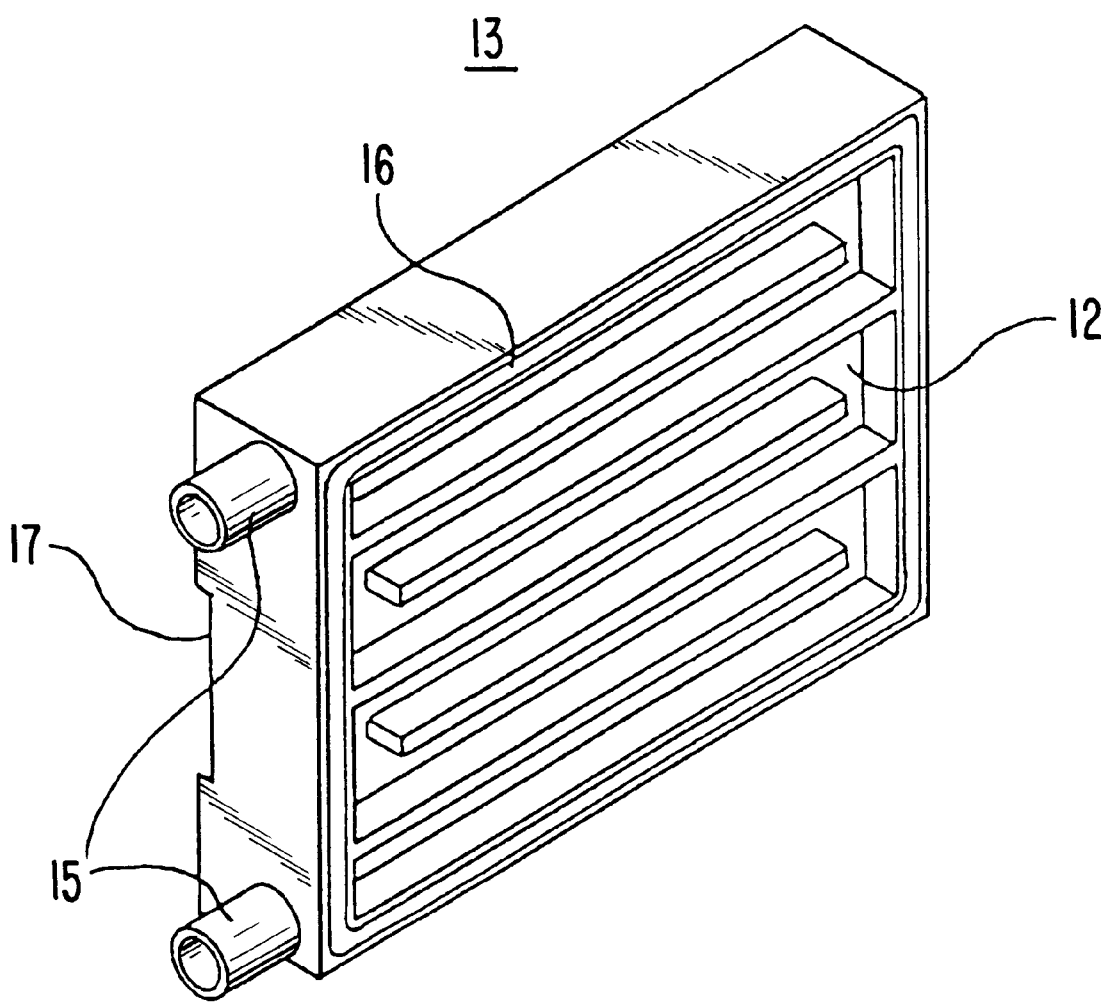
FIG. 3 depicts a view of the jacket of the electrophoresis system shown in FIG. 1.

Then, detailed description will now be made of the temperature control means of the glass plate and gel during electrophoresis, in accordance with the present invention. On the external faces of the glass plate 2 and the notched glass plate 3 cramping the gel 1 are pressed and closely attached jackets 13, 13 with channels 12 open toward the glass plates by means of cramps 14, 14. Acrylic resin is used as the raw material of the jacket 13, so the jacket has good thermal insulating potency against outer atmospheric temperature. Because the jackets are transparent, the coolant flow can be checked and the mobility of a sample during electrophoresis can be identified, with reference to dye such as bromphenol blue simultaneously electrophoresed. FIG. 3 depicts the detailed view of the jacket 13. The jacket 13 has two sets of joints 15, 15 arranged, whereby channel 12 is formed in a snaking fashion to connect the individual joints 15, 15 together. Then, sealing material 16, preferably silicon sponge, is arranged on the outer circumference of the formed channel 12. As shown in FIG. 2, the cross sectional shape of the channel 12 is rectangle, with a dimension of a 14-mm width and a 6-mm depth as one example. The dimension of the channel serves as a factor determining the coolant flow rate. When it is intended to increase the flow rate and to increase the heat conductivity, the cross-sectional area of the channel should be designed to be smaller. The channel shape is not limited to rectangle, and the distance of the wet circumference to the cross-sectional area should be designed smaller, to raise essentially the heat conductivity. For example, therefore, a semi-circular cross-sectional shape is also effective. On the face opposite to the face with the channel 12 formed thereon is arranged engaging groove 17 on the jacket 13, which can be engaged in the cramp 14 described below.

Figure 4:
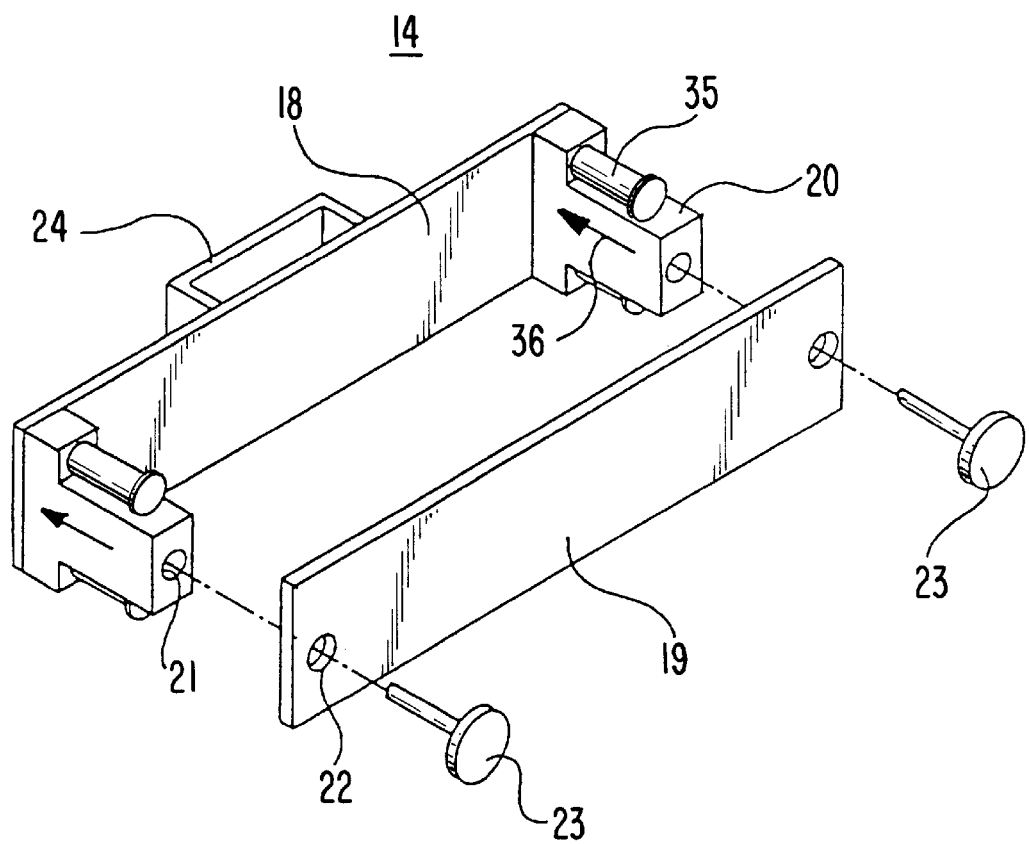
FIG. 4 depicts a view of the cramp fixing the jacket shown in FIG. 4 onto the glass plate.

FIG. 4 is a detailed view of the cramp 14. The cramp 14 comprises plate 18 of a metal material and press plate 19. On both the ends of the plate 18 are arranged blocks 20, 20 exerting elastic force along arrow direction 36 via spring material 35. Inside each of the blocks is mounted female screw 21. Alternatively, on the press plate 19 are arranged bolt holes 22, 22 corresponding to the positions of the female screws 21, 21 in the block 20, and if the bolts 23, 23 are inserted and rotated into the bolt holes 22,22, the bolts 23, 23 are engaged with the female screws 21, 21, to make a combination of the plate 18 with the press plate 19. Additionally, the cramp 14 functions to fix the electrophoresis unit, such as gel 1 and glass plate, on a supporting table, and holder 24 is arranged on the face of the plate 18 which is not facing the press plate 19.

The positional structures of the gel 1 and the glass plates 2, 3 cramping the gel, the jacket 13 and the cramp 14, are shown in the cross-sectional view of the present system of FIG. 2, and these are integrated together as one electrophoresis unit by means of the cramp 14. The integration of the electrophoresis unit is done as follows.

The plate 18 in the cramp 14 is placed on a table, while the holder 24 is held on the back. One jacket 13 is arranged while the engaging groove 17 is held downward so that the jacket might be engaged in the plate 18. Subsequently, a pair of the glass plates holding the gel between the plates are arranged above the jackets 13, 13 so that their centers are matched to each other. Then, the other jacket 13 is arranged above the glass plates while the engaging groove 17 is held upward. Subsequently, the press plate 19 is arranged above the jacket 13 to be engaged in the engaging groove 17. Then, the bolt 23 is engaged, through the bolt hole 22 of the press plate 19, into the female screw 21 of the block 20.

By the above procedures, the position of the plate 18 and one jacket 13, the position of the jacket 13 and the glass plate, and the position of the press plate 19 and the other jacket 13 are fixed at specific positions, depending on the engagement of the screw parts. So as to fix the plate 18, the individual jackets 13, the glass plates and the press plate 19, the bolt 23 is rotated and engaged into the female screw 21. When the glass plates are interposed between the individual jackets 13, 13, the distance of the engaging grooves 17, 17 arranged in the jacket 13 is configured to be longer than the length from the inside of the plate 18 to the top end face of the block 20. As the rotation of the bolt 23 progresses, however, the sealing material 16 is firstly collapse elastically to closely attach the glass plates and the jackets 13, 13 together; by further such rotation, the block 20 sifts in an opposite direction to the arrow direction 36 to be drawn toward the plate 19. The contraction of the spring material 35 then works as spring elastic force, which serves as an attracting power between the plate 18 and the press plate 19. Thus, the jackets 13, 13 and the glass plates, arranged between them, can be fixed at a predetermined position.

The cramp composed of a pair of the plates has an action holding the jackets onto plates, and the holding force works along the direction of the gel thickness, so the sealing material can be pressed against the plates. Because the coolant flowing in the jackets has a velocity energy, additionally, the jackets can be pressed, in the direction against the force, onto the plates. Because the cramp and the jackets are in contact via their faces to each other, additionally, these holding force can be uniformly transferred to the jackets, and therefore, the force can work uniformly on the gel face, with no resultant distortion of the gel thickness. Because the cramp material has greater rigidity than that of the jacket material, furthermore, the contact face does not curve via these pressing force, so that the pressing force can work more uniformly on the external faces of the jackets. Because the cramp has a structure such that the jackets are cramped and held onto the external faces of the two plates, still further, the number of necessary parts is less, advantageously for good handleability. Because the jackets and the cramp are configured in an engaging structure, the positioning is readily done and their contact is composed of their face contact and the contact between the depth face of the engaging channel and the plate face along the thickness. They are more intensely held together in this structure.

In the electrophoresis unit thus fixed, square flow pass 28 is formed between each of the individual jackets 13, 13 and each of the individual glass plates, as shown in the cross section of FIG. 2. As shown in FIG. 1, additionally, by connecting tube 29 to the joint 15 and thereafter arranging a coolant circulating unit (not shown in the figure) equipped with a temperature control function, circulating coolant controlled to an appropriate temperature can flow in the electrophoresis unit. Because the channel formed in the jacket is of a snaking form on the both sides of the gel plate, effective temperature control can be done with the equal heat exchange efficiency. As shown in FIG. 2, further, the sample groove 4 is positioned to hold the glass plate and to be held between the channel 28, and furthermore, the sample groove 4 can retain the sample filled in the groove at an appropriate temperature. As shown in the arrow 30 in FIG. 1, the flow direction of circulating coolant into the formed channel 28 is structured such that the flow starts from the bottom part of the jacket 13 on the side of the back face of the gel plate and flows through the channel 28 out of the joint 15 in the upper part of the jacket 13, and then flows in the bottom part of the jacket 13 on the side of the front face and flows through the channel 28 out of the upper part of the jacket 13, and the flow then returns into the coolant circulating unit equipped with the temperature control function. Because the coolant flow starts from the bottom part of the jacket as has been described above, the air inside the flow pass at the initial stage can be purged to realize stable liquid flow. The material of the tube 29 is preferably silicon rubber.

In the electrophoresis system, the coolant circulating unit equipped with the temperature control function is used, which can control the temperature of coolant flowing in the jacket 13 and can circulate the coolant as well, but these functions may be independently used. In the example, temperature control is effected in such a way that the temperature of coolant pooled in the coolant circulating unit equipped with the temperature control function is detected with a temperature sensor for subsequent heating or cooling the coolant to the objective temperature. In this case, the difference in temperature between the pooled coolant and the coolant flowing in the jacket may develop due to the influence of room temperature and the like. If the temperature sensor structurally detects the coolant temperature in the jacket in such case, more effective control of the temperatures of the glass plates and the gel can be practiced. Also useful is another method comprising winding an insulating material such as silicon sponge foam around the individual tubes to countermeasure against the increase of the temperature change of the circulating coolant in the route from the coolant circulating unit equipped with temperature control function to the electrophoresis unit. Because not buffer solution but coolant such as water and 10 to 30% v/v ethylene glycol is used as the coolant, the coolant is not costly but can be recycled, being safe with no problematic electricity leakage.

In FIG. 1, "31" is supporting table and is of the shape of character L as shown in the cross-sectional view of FIG. 2. On the vertical face of the character L are arranged holder 24 arranged on the cramp 14 and engaging hook 32; while on the horizontal face of the character L is arranged guide 33 so as to mount the lower buffer solution tank 7 at a predetermined position. When the electrophoresis unit fixed on the supporting table 31 is set via the engagement of the holder 24 and the hook 32, the electrophoresis unit can be fixed at one position. In the electrophoresis unit, the lower end part of the glass plate 2 is in contact to the lower part buffer solution tank 7, to structure supporting block 38 to avoid the loading of the whole weight of the electrophoresis unit over the hook 32.

In the following example, the DNA analysis described in Japanese Patent Laid-open No. Hei 06-30797 and Japanese Patent Application No. Hei 06-709 is conducted using the present invention. DNA samples are not limited to the DNA described in the example. The present invention is effectively applicable to a variety of DNA regions including a site of DNA polymorphism and a mutation site.

In the present example, so as to elucidate the personal difference in the sequence of the HLA (human leukocyte antigen)-DQA1 region, the region is analyzed by the asymmetric PCR-SSCP method. The asymmetric PCR-SSCP described in the present example is a modified PCR-SSCP.

The DNA extraction and purification process from a biological sample was carried out according to the method described in the Japanese Patent Application No. Hei 06-709. According to the method, genomic DNA of about 1 $\mu$g was recovered from the whole blood (50 $\mu$l), which was dissolved in TE buffer (100 $\mu$l). As an another method, a method using a genomic isolation kit (manufactured by Behrlinger Mannheim) is also illustrated. The method described in the Japanese Patent Application No. Hei 06-709 is not intended to be limiting. The method using the whole blood as a biological sample is described herein, but DNA may be extracted from any biological sample, such as hair tissue cells, for use in the following procedures.

PCR amplification of DNA for the target DNA region was conducted according to the method described in the Japanese Patent Application No. Hei 06-709, which is not intended to be limiting. In the present example, however, GH26 was preliminarily labeled at position 5' with rhodamine x isothianate (XRITC) for use as one of the primers. According to this method, the DNA in the region was amplified from the genomic DNA of about 100 ng, to a final yield of about 1 pmol.

After the PCR amplification, the reaction solution of 2 $\mu$l was collected and mixed with the charging solution (2 $\mu$l; 98% formamide, 20 mM EDTA, 0.05% bromphenol blue, 0.05% xylene cyanol) for preparing a sample for electrophoresis.

Description will now be made about the gel for use in separation. As to the gel, a 17 w/v % (acrylamide:bisacrylamide=99:1) acrylamide stock solution containing TBE buffer (89 mM Tris-HCl, pH 8.30, 89 mM borate, and 2.5 mM EDTA) was firstly degassed, followed by mixing the solution with TEMED (tetramethylethylenediamine) to a final concentration of 0.07% and APS (ammonium persulfate) to a final concentration of 0.06% under agitation, and the resulting mixture was then poured in a space structured by a pair of glass plates and spacers (19-cm width×15-cm application distance×0.35-mm thickness), prior to insertion of a shirk comb and subsequent polymerization. The aforementioned reagents were all available from Nakarai Tesque Co., Ltd. The glass plates retaining the gel were arranged in the electrophoresis system described above.

The electrophoresis conditions are now described below. As an electrophoresis power source, a unit commercially available from ATTO Company (Type AE 3131) was used; as a coolant circulating unit with temperature control function, a unit commercially available from Pharmacia (Type Multitemp) was used. The coolant circulating unit had the performance of a flow rate of 10 liters/min; the temperature range was set from $-10°$ C. to 90° C.; and temperature control was conducted at a precision of $\pm 0.1°$ C. Connecting the power source to the electrodes of the buffer solution tanks, preliminarily, predetermined electric field is applied prior to charging the prepared sample into the gel groove (preliminary electrophoresis). The conditions of preliminary electrophoresis are such that the water temperature flowing in the jacket is set to 20° C. and that a 400-V constant voltage is applied for 60 minutes. Subsequently, the prepared sample was charged followed by applying electric field for separation(electrophoresis). The electrophoresis conditions are such that the temperature of coolant flowing in the jacket is set at 20° C. and a 600-V constant voltage is applied for 400 minutes at an electrophoresis voltage (a value of the applied voltage divided by application distance) of 40 V/cm. The current level then was 16 mA at maximum.

After appropriate duration of electropheresis, the glass plates were drawn out from the unit, and the stain of the glass plates was wiped off. The plates were then arranged on the detection surface of the fluorescent detector (FM-Bio; manufactured by Hitachi Soft, Co., Ltd.), to detect the fluorescence of XRITC used to label the primer for analysis.

Figure 5:
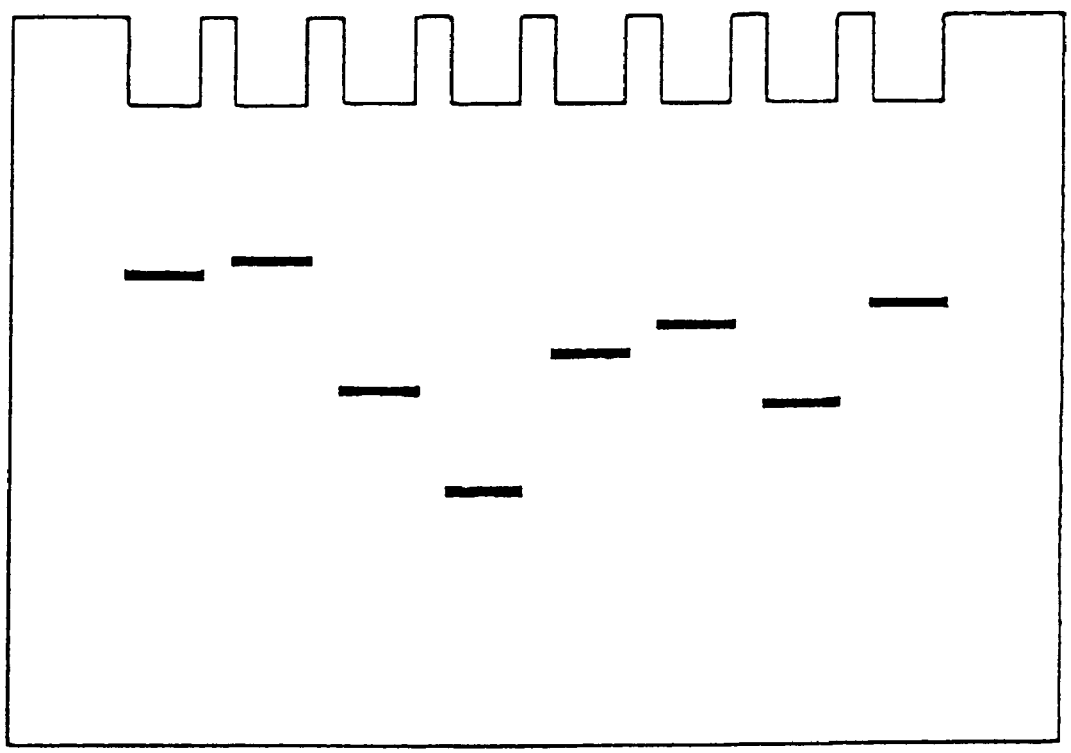
FIG. 5 depicts a view of the results of SSCP on the electrophoresis system of the present invention.

FIG. 5 is a typical view depicting the analysis results in accordance with the present invention. (1) and (8) depict the electrophoresed single-stranded DNA of the sense strand of the HLA-DQA1, corresponding to the individually separated polymorphism patterns. All of these samples were determined of their types by preliminary DNA sequencing, which are all homozygous samples of types 0101, 0102, 0103, 0201, 0301, 0401, 0501, and 0601. In the present example, it is indicated that eight types of the DQA1 region individually separated have independently different mobilities, depending on the difference in the sequence of each type. The separation results are the same as the separation results described in Biophysics and Chemistry (Journal of Nippon Electrophoresis Association), Vol.38, pp.94, 1994. The experimental procedures described in the Journal of Biophysics and Chemistry were carried out by using the same type of electrophoresis system as the prior art system described in Japanese Patent Laid-open No. Sho 57-163861; in other words, the results are shown when temperature control is effected by means of one of the glass plates supporting the gel. The temperature difference "T0–Tw1" in the gel during electrophoresis is assumed to be 0.01° C. under the experimental conditions, by using the formulas 1 and 2. On contrast, the temperature difference by the single-sided temperature control as the conventional art is assumed about 4-fold that of the double-sided temperature control.

Under the electrophoresis conditions in the experiments described above, the electrophoresis voltage generates less Joule's heat, with a smaller temperature difference in the gel below 0.1° C. It is indicated that at such low electrophoresis voltage, the electrophoresis system of the present invention can effect separation like those of the conventional methods. The separation characteristics of the present invention are markedly demonstrated at a higher electrophoresis voltage.

By the same analysis using the same sample as shown above except that the applied voltage and the electrophoresis duration were modified among the electrophoresis conditions, separation was effected. In FIG. 5 depicting the results at an electrophoresis voltage of 600 V (40 V/cm) and an electrophoresis duration of 400 minutes, the individual DNAs are independently separated. Hence, each mobility distance of each of the DNAs may satisfactorily be gained by the product of an applied voltage and an electrophoresis duration; therefore, an electrophoresis duration should be 200 minutes, given an applied voltage of 1200 V (80 V/cm). Then, by using the system (single-sided temperature control) described in J. Climat. and the system described in the present example, separation was effected independently. The preliminary electrophoresis then was done at 800 V for 60 minutes. The maximum current level at 1200 V applied was 25.8 mA in the present system, while the level was 26.7 mA for the single-sided control.

Figure 6A:
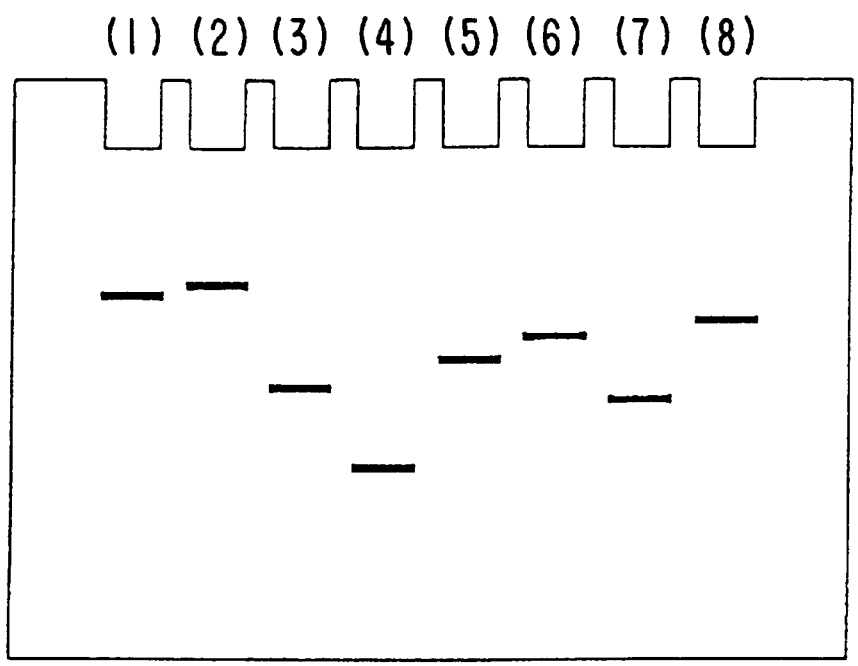
FIGS. 6 (A) and (B) depict each of views of the results of SSCP on the electrophoresis system of the present invention and on the conventionally shown electrophoresis.
Figure 6B:
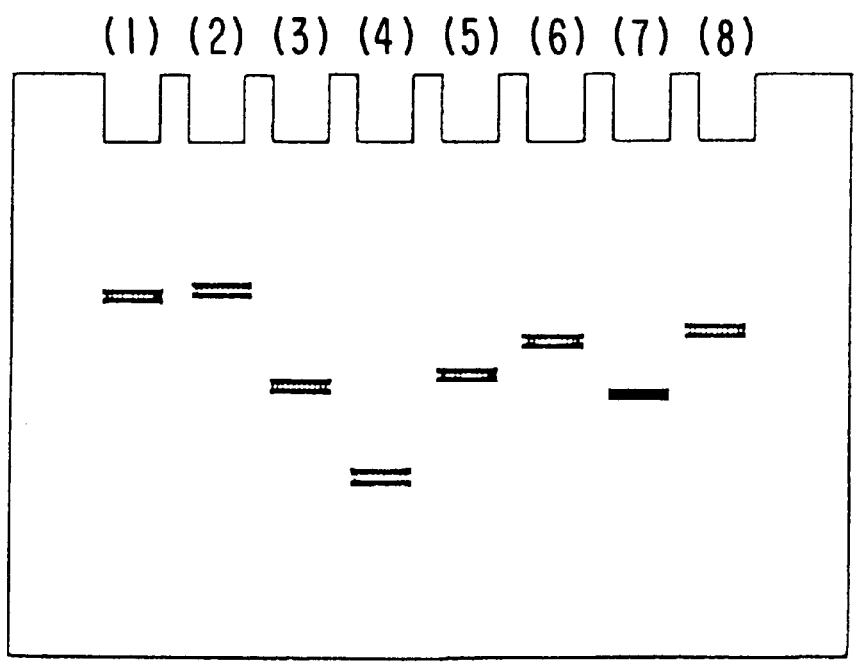

FIG. 6 (A) schematically depicts the separation results on the system described in the present example; FIG. 6 (B) schematically depicts the separation results by the conventional method. In FIG. 6(B), it is observed that the separated DNAs have a larger band width; and it is observed further that a DNA band may possibly be separated into two DNA bands on the basis of dense and pale colors of the band. In FIG. 6(A), alternatively, the separation results are almost the same separation patterns shown in FIG. 5, and the width of the DNA bands is observed sharper than that shown in FIG. 6(B). The reason whey these difference in the results may occur will be discussed hereinbelow.

By using the fundamental formulas collectively shown in the Section "Operation" under individual electrophoresis conditions, the temperature difference in the gel, namely "T0–Tw1" and the difference between the temperature of the glass plate facing the gel, namely "Tw1" and the temperature of the plate facing water flow, namely "Tw2" were determined, to estimate the maximum temperature "T0" of the gel vs. the water flow temperature "Tw2".

Firstly, the flow "v" was determined on the basis of the flow (10 liters/min) of the coolant circulating unit and the shape of the channel 28 (channel width (1.4)×depth (about 0.66 mm)), which was 1.80 m/s. Furthermore, the representative length "Ls" of the channel 28 was 0.88 cm and the dynamic viscosity coefficient of water at 20° C. was 1.011× $1/10^6$ m$^2$/s. Using then the formula 5, the Re number was determined as $1.6\times10^4$. Because the Pr number of water at 20° C. was 7.11, the Nu number was then determined as 80.7, using the formula 6. The heat conductivity of water at 20° C. was 0.594 W/m$^2$.K, and using the formula 7, the heat conductivity "h2" was $5.4\times10^3$ W/m$^2$.K. Based on the gel area, the heat flux "q" is represented as G(W)×0.057 (1/m$^2$); provided that glass plate thickness of 5 mm, glass plate heat conductivity of 1.35 W/m$^2$.K along with the value of "h2" are given into the formula 4, the formula "Tw1–Tw2" can be represented as a formula of heat generation G(W) under various electrophoretic conditions in accordance with the present invention. By the conventional method by single-sided control, alternatively, the value is approximately 2-fold that of the present invention. The values of "T0–Tw1" and "Tw1–Tw2" are individually estimated, given the applied voltage of 80 V/cm, and the values are also estimated, given 40 V/cm. They are collectively shown in Table 2.

TABLE 2

|  | Electrophoresis conditions | Joule's heat (w) | T0– Tw1 (k) | Tw1– Tw2 (k) |
| --- | --- | --- | --- | --- |
| Present invention | 40 V/cm | 9.6 | 0.02 | 0.65 |
| Conventional method | 80 V/cm | 32.0 | 0.03 | 4.81 |
| Present invention | 80 V/cm | 31.0 | 0.08 | 2.10 |

The results are discussed and described below. When the electrophoresis voltage was preset to 80V/cm higher than 40 V/cm as the conventional applied voltage, the applied voltage was 2-fold but the generation of Joule's heat was increased 3- fold. The increased heat energy kept the gel temperature high during electrophoresis, and the separation results possibly reflected the additive sum of the coolant temperature, the increment of the gel temperature and the temperature difference between both the sides of the glass plate. For single-sided temperature control, thus, the temperature difference of 4.8° C. was added to the water temperature, which brought about the separation results at an assumed gel temperature of about 25° C. For double-sided temperature control in accordance with the present invention, alternatively, the temperature difference was observed to be 2° C. Consequently, the separation then was assumed to be conducted at a gel temperature of about 22° C. The reason why the assumption is reasonable will be validated below.

Figure 7:
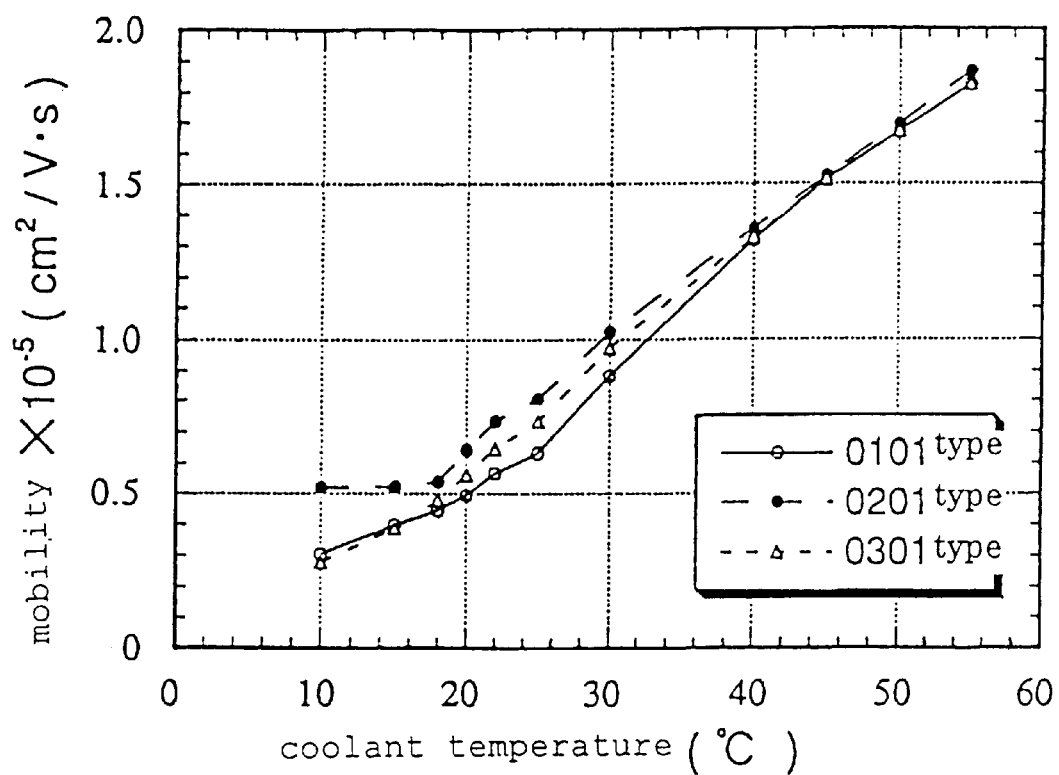
FIG. 7 depicts a view of the separation results on the electrophoresis system of the present invention, when the coolant flow temperature is changed.

Using the same gel and the same sample for the same duration, FIG. 7 shows the results of separation at a variable water temperature within a range of 10° C. to 55° C. and an applied voltage of 40 V/cm at which the generation of Joule's heat was less. The axis of abscissa represents coolant temperature, while the axis of ordinate represents mobility (a value of mobile rate divided by applied voltage). The results of types 0101, 0201 and 0301 of the HLA-DQA1 region are plotted. The results indicate that as the coolant temperature is higher, the mobility is also increased. The slopes of the graphs indicate the relation of the mobility of nucleic acid sample with temperature, but accurately speaking, the slopes represent the observed results of the change of the conformation of a nucleic acid sample, depending on the temperature, in combination with the influence of the change of the gel viscosity on the mobility, depending on the temperature. The slopes of the mobility of individual samples around 20° C. are about 7%/°C. on average. As the results of experiments of double-sided temperature control, the mobility was compared at electrophoresis voltages of 40 and 80 V/cm, corresponding to the conditions providing the results shown in FIG. 5 and FIG. 6(A). The mobility was increased by about 15%. Taking consideration of the temperature increment of 2.1° C., then, the increment of the mobility was 7.4%/°C., which agrees very well with the value shown in FIG. 7. Therefore, the reasonableness of the fundamental formulas as regards heat conduction can be validated.

In FIG. 6(B) showing the results of the conventional method, the DNA band gets wider, which may possibly be due to the temperature difference in the gel. Herein, the temperature difference cannot be accurately estimated, but approximately, the difference is 4 -fold in the gel that of the double-sided temperature control. The temperature difference between water flow in the thermostat plate and the gel is 2-fold that of the double-sided temperature control, so the effects thereof may possibly change the mobility of these samples consequently. In the present example, experiments were carried out under conditions such that the gel temperature might be equal or higher than outer atmospheric temperature, so discussion was made following the heat flow shown in FIG. 10(B). Practically, however, some case may be present wherein the heat source of outer atmospheric temperature is greater than the heat generation of gel, for example, a case at atmospheric temperature which requires to preset gel temperature to 4° C., the heat flow then is more difficult to be analyzed. For double-sided temperature control, alternatively, an experimental system with no influence of outer atmospheric temperature on gel temperature can be provided. Therefore, the present invention is advantageous from such respect.

The above results indicate that the gel temperature during electrophoresis can be accurately estimated using the system of the present invention, thereby certifying the reproducibility of the experiments at a higher precision. When a higher applied voltage is preset, additionally, the generated Joule's heat is highly efficiently exchanged so that the increase of the gel temperature can be reduced compared with single-sided temperature control, which indicates that the temperature influence on the separation can be reduced. Thus, a higher applied voltage can be applied, to shorten the electrophoresis time required for separation.

An another advantage of the present invention will further be described below. It is indicated as described above that a higher applied voltage can shorten the separation time by the electrophoresis method. So as to further shorten the electrophoresis time, a still higher applied voltage was preset for experiments and investigations using the present system. The method is approximately described as follows. As shown in the Section "Operation", the difference in the gel, namely "T0–Tw1" and the temperature difference "Tw1– Tw2" between both the sides of the plate are approximately calculated, on the basis of the applied voltage and the consequent current level and the temperature of the coolant flowing on the external face of the plate, to control the temperature of the coolant flowing in the jacket so as to maintain the gel temperature at an appropriate temperature, and electrophoresis is thereafter carried out.

By the same analysis method using the same sample, the applied voltage at 2400 V (160 V/cm) gives an electrophoresis time of 100 minutes. Then, separation was effected using the system described in the example. Then, the preliminary electrophoresis conditions were 1600 V and 60 minutes. Given the electrophoresis voltage at 160 V/cm, the gel temperature difference was estimated to be 0.3° C., while the temperature difference between both the sides of the glass plate was estimated to be 9.3° C. So as to preset the gel temperature during electrophoresis at 20° C., the water flow was set at 10.7° C. for electrophoresis.

The results of separation under the electrophoresis conditions are the same as the results shown in FIG. 6 (A) and FIG. 5 depicting the results of double-sided temperature control. More specifically, the gel temperature during electrophoresis was maintained at 20° C. as preset, even when electrophoresis was carried out at a high applied voltage 4-fold that of conventional one for a short electrophoresis time ¼-fold. Thus, separation can be carried out under objective electrophoresis conditions. By the method described above, therefore, it is indicated that the electrophoresis time can be shortened.

In the present example, a symmetric PCR-SSCP is described where the gel temperature control during electrophoresis is considered very important for sample separation, but the present invention is not limited to the example. For example, the present invention is also suitable for PCR-SSCP capable of detecting mutant gene or for the electrophoresis for DNA sequencing represented by the Sanger method. Additionally, the gel composition is not limited to polyacrylamide and the like, but the present invention is also applicable to gel electrophoresis using agarose and the like. Furthermore, the present invention is not limited to those described above, but is also applicable to the separation of biological protein samples by electrophoresis. For example, the temperature of a gel with higher separation potency during SDS (ammonium ? sodium dodecyl sulfate)-containing acrylamide gel electrophoresis can be maintained so appropriately for separation of protein samples. Because the sample groove can be temperature controlled, the groove can be controlled to the reaction temperature even after a sample is placed, for subsequent practice of electrophoresis.

The present example describes a method to control the gel temperature during electrophoresis appropriately by a process comprising recirculating the heating medium as a heat transfer means, but the same effect can be realized by any heat transfer means attaining at least 103 W/m².K or more, as in the present example. One example of the method comprises configuring a heat exchange plate including a heat-conductive device as the jacket described in the present example, but so as to increase the heat conductivity, a certain arrangement is necessary, such as the use of grease between the plate and the heat exchange plate so as to elevate the heat conductivity. Additionally, another arrangement may be required to prevent the damage of the heat transfer plate due to electricity pass from electricity leakage.

Figure 8:
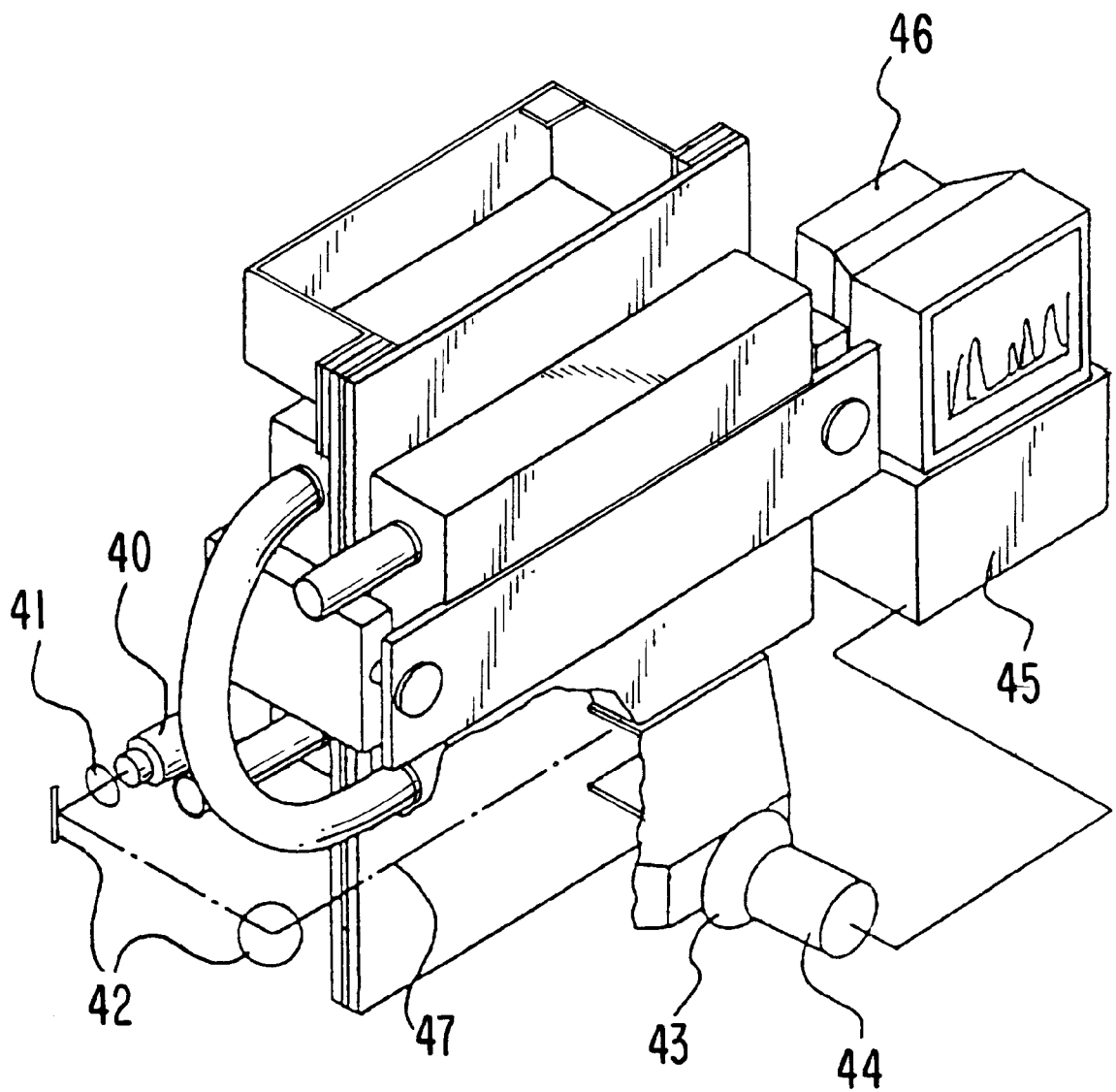
FIG. 8 depicts one example arranging a detection mechanism on the electrophoresis system of the present invention.

Another example of the present invention will be described below. In the example described above, the system is explained only as a machine effecting separation for electrophoresis, and therefore, the sample should be detected and analyzed by some means after electrophoresis. FIG. 8 incorporates those described above collectively. The system shown in the figure can efficiently effect separation, detection and analysis. The structure concerning separation and temperature control such as glass plate and cramp is common to those shown in FIG. 1, but the following structure as the detection mechanism is further arranged in the system. The detection mechanism is composed of laser 40 emitting a specific wave length, collimating lens 41 collimating a laser beam, mirror 42, polar screen 43 and phototube 44.

Computer 45 as an analysis mechanism incorporating the electric signal generated in the phototube 44 and monitor 46 thereof is arranged, to effect the analysis of the separated products by transforming an electric signal into image data. Samples for the system should be preliminarily labeled with a fluorescent substance selected as appropriate for the excitation beam, for example fluorescein isothianate (FITC) for argon laser and texas red for helium-neon laser.

Figure 9:
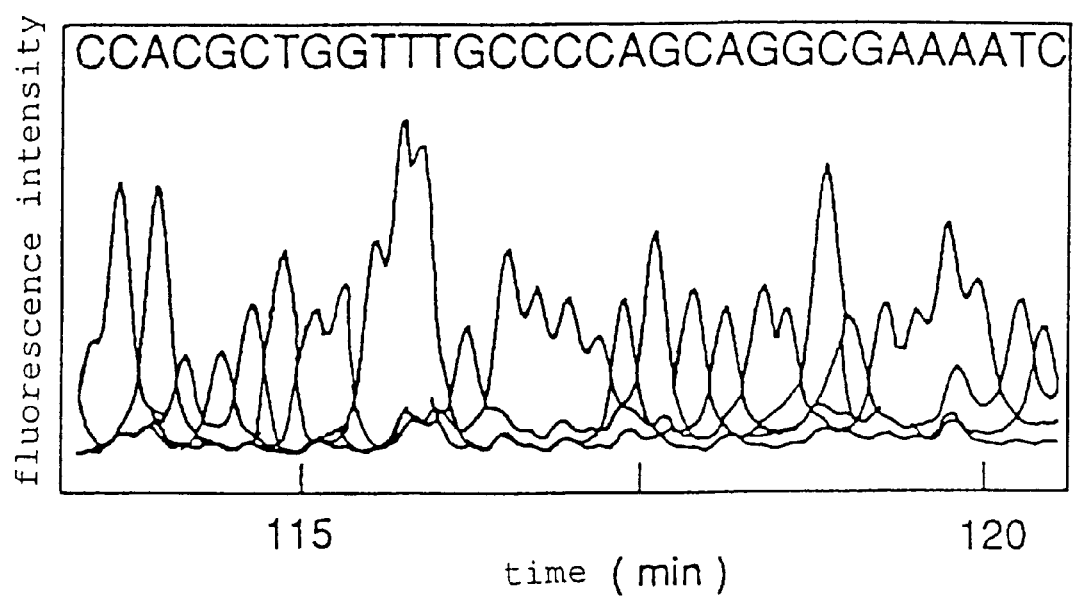
FIG. 9 depicts a view of the results of DNA sequencing on the electrophoresis system of the present invention.

So as to reduce the background during detection, the structure described above is placed at a dark chamber predetermined applied voltage and an electrophoresis time, and thereafter, the temperature of coolant flow can be set to the highly separable gel temperature during electrophoresis to carry pout electrophoresis. Then, the sample filled in the gel groove is electrophoresed in the gel region (separation zone) strictly temperature controlled, until the sample reaches an excitation beam-irradiated detection zone with a detection window to emit fluorescence in the increasing order of sample mobility, which is then received and detected on the phototube. The detected signal is incorporated into a computer over time, to be then transformed into image data and numerical data for use as sample separation data. Using the system, DNA sequencing was conducted. As to the method, using a sequencing kit (Code M13-110; manufactured by Toyobo) containing a template and an enzyme produced by modified T7 polymerase as the reagent and the protocol according to the instruction attached, the reaction is progressed. The resulting reaction solution is charged in the system to effect separation at a given electrophoresis voltage of 200 V/cm to set the gel temperature to 55° C. Some of the results are shown in FIG. 9. The axis of ordinate represents fluorescence intensity, while the axis of abscissa represents the time of electricity pass; in the upper part of the figure, the order of nucleotide sequence is shown. Four-hundred nucleotides could be detected 120 minutes later, to yield good nucleotide sequence data. The electrophoresis conditions are such that the electrophoresis time is about ¼-fold the separation time required for general DNA sequencing, so the conditions can enable extremely high-speed separation. As has been described above, a detection system detecting an electrophoresing sample in the gel, if arranged in the present system, can determine the mobility of the sample separated under strict temperature control during electricity pass.

For the system of the present embodiment I, counter measures such as arrangement of covers so as to prevent the touch of anything during electrophoresis or counter measures to switch off electricity in the occurrence of electricity leakage due to an event are useful.

Thus, the present embodiment I has been described with reference to the specific preferable embodiments of the present invention by way of illustration, which are not intended to be limiting, obviously for skilled person in the art.

In accordance with the present embodiment I, the gel during electrophoresis can be temperature controlled and retained appropriately, and separation can be realized under conditions without non-uniform temperature distribution in the gel such as smiling. Therefore, a biological sample is highly separated. Compared with single-sided temperature control as the conventional method, the present invention can generate environment with a smaller temperature difference along the direction of the gel thickness, so separation can be done with less distortion such as the occurrence of enlarged DNA band width as observed conventionally. Compared with single-sided temperature control, the present invention is configured to have a higher heat exchange efficiency. Thus, the invention can allow the increase of the generation of Joule's heat, so a higher electrophoresis voltage can be applied, whereby the separation time at a high speed can be realized.

Embodiment II

The embodiment II will now be described in detail in specific examples. In the example, the gel including an excitation beam-irradiating part should be wholly temperature controlled at a higher efficiency, throughout electrophoresis and detecting. Even under high voltage application, the gel temperature can be maintained at an objective level strictly over the overall duration of electrophoresis; additionally, in order to realize a feedback control of the gel temperature, a power source element can detect the power level, and based on the power level, the temperature of temperature control unit is calculated to control the gel temperature at a predetemined temperature by using a given calculation formula and calculation parameters.

Furthermore, description will follow about an example where the occurrence of mildew is prevented on the signal light passing area and slit Inner face of the plate and on the body of the electrophoresis system including the temperature control units.

More specifically, during electrophoresis in a high electric field, the pH of a buffer solution changes through the electrolysis of the solution, resulting in the change of the heat generation even at a constant voltage applied, so that the gel temperature is inconveniently departed from the objective level. In addition, when the gel temperature is to be adjusted to a low temperature, mildew generates on the glass face outside the temperature control region by means of the temperature control units, which works as an obstacle against detection or which causes electricity leakage. These problems are effectively solved in the present example.

Examples

Figure 12:
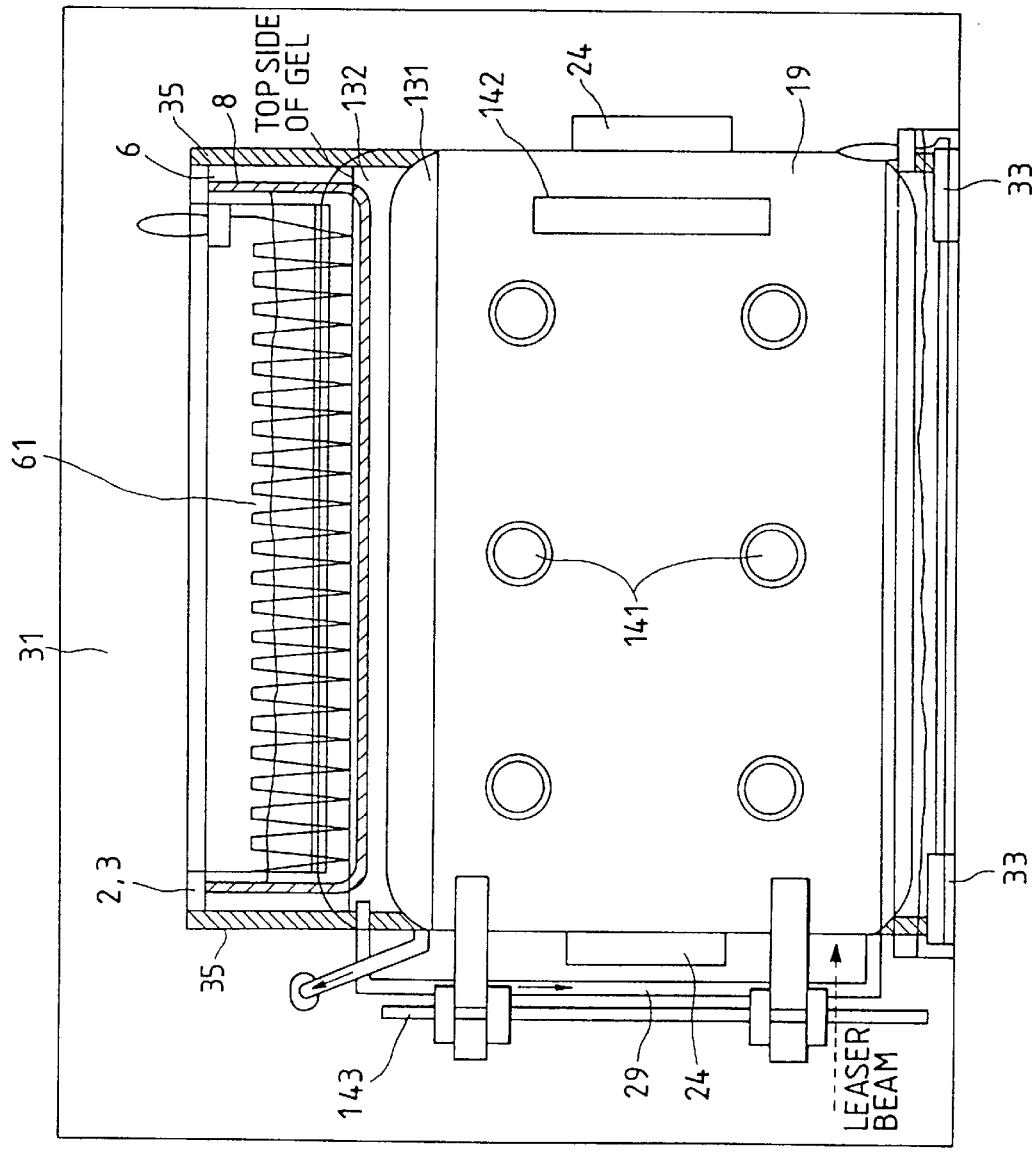
FIG. 12 depicts a schematic view of a part of the electrophoresis unit of the automatic fluorescent electrophoresis system.
Figure 13:
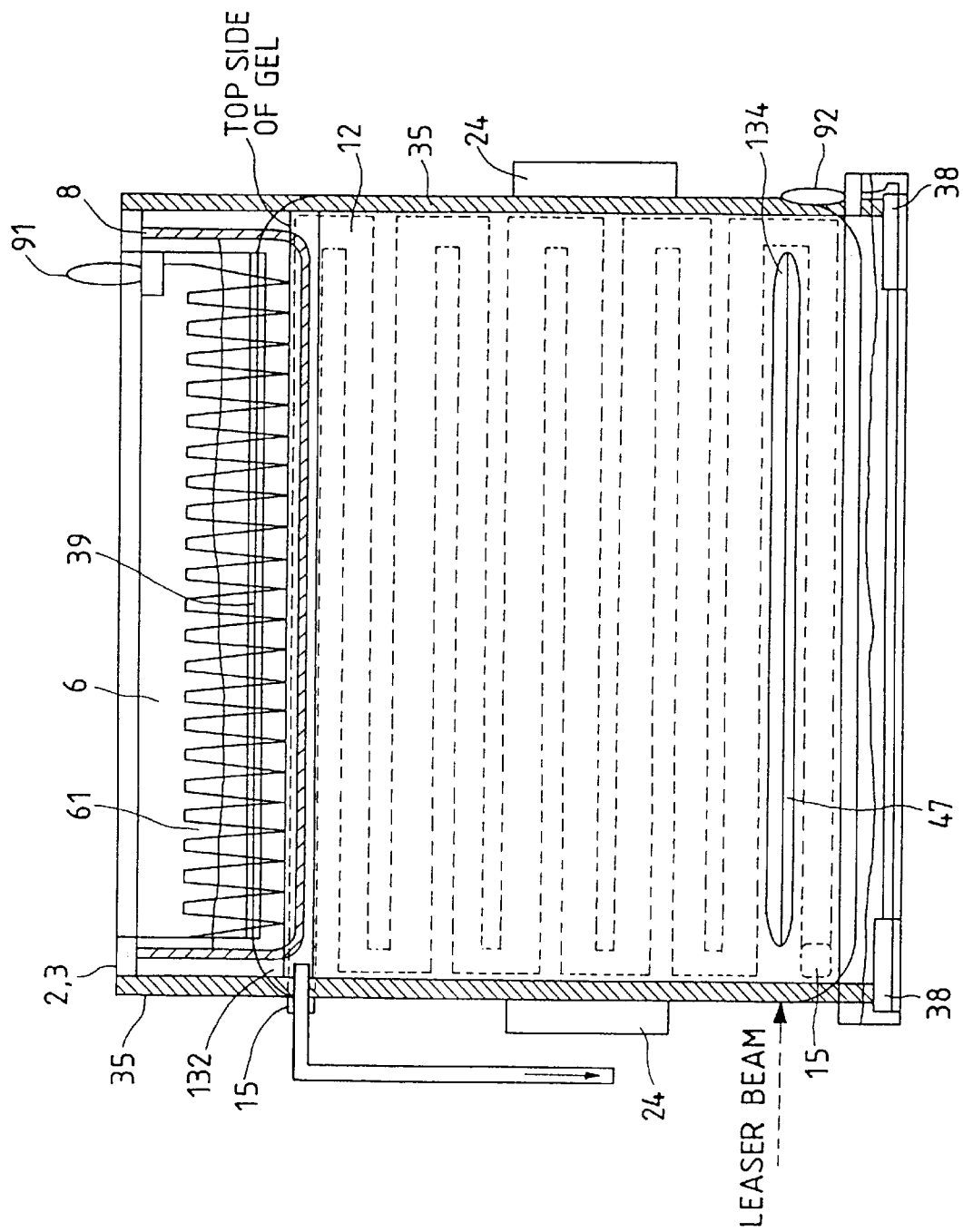
FIG. 13 depicts a schematic view of a part of the electrophoresis unit of the automatic fluorescent electrophoresis system (partial view)
Figure 14:
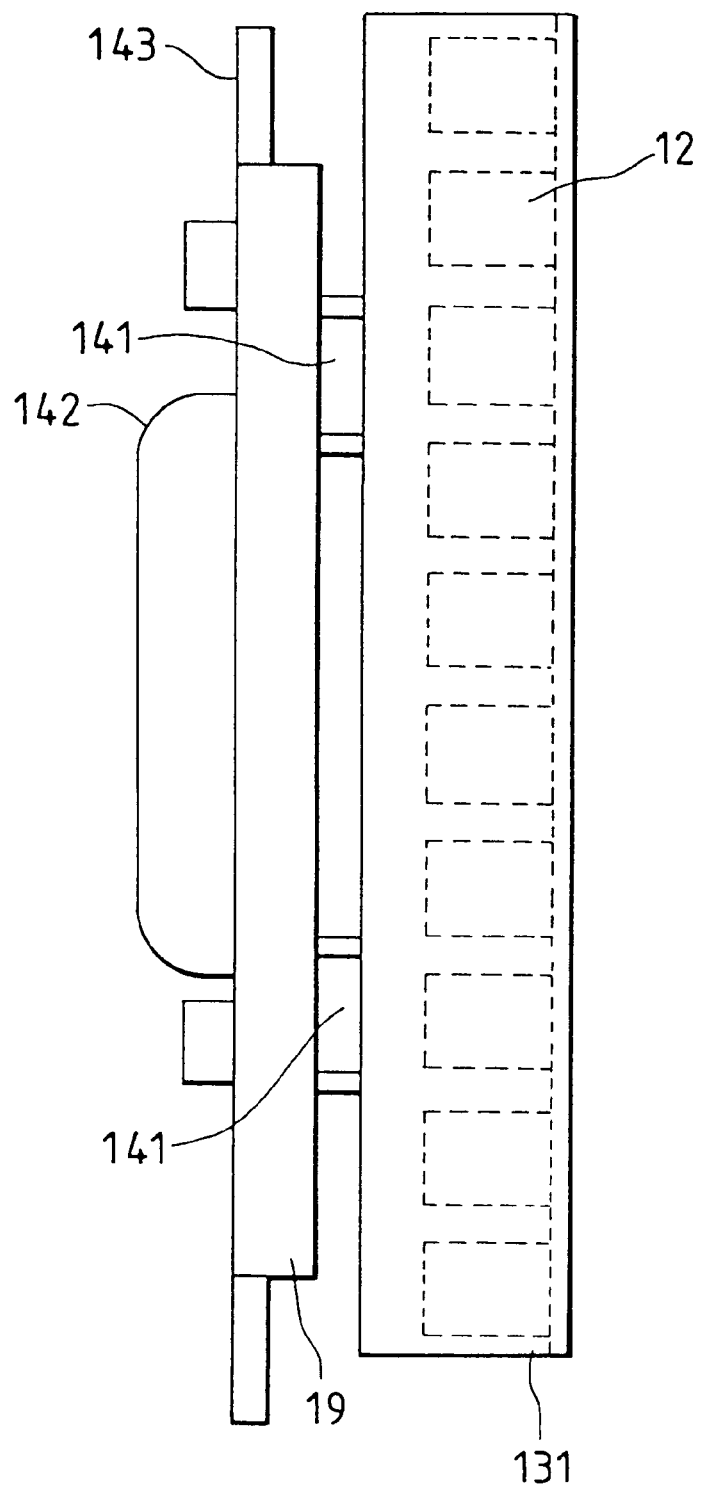
FIG. 14 depicts a schematic view of a part of the electrophoresis unit of the automatic fluorescent electrophoresis system (partial view)

FIG. 11 depicts a cross-sectional view of the schematic structure of an automatic fluorescent electrophoresis system as one example of the present invention; FIG. 12 depicts the front view of a part of the electrophoresis unit including the temperature control units; FIG. 13 depicts a view of a part of the electrophoresis unit from which the temperature control jacket is removed; and FIG. 14 is a side view depicting the relation between the temperature control jackets on the front side of the electrophoretic part and the press plate.

As the gel material to be used in the example of the present invention, use may be made of general gels such as polyacrylamide. Additionally, so-called gradient gels or gels with modified levels of denaturing agents may satisfactorily be used as well.

The automatic fluorescent electrophoresis system relating to the example of the present invention is composed of body part 100, the gel electrophoresis part 200 on the front face thereof and control unit 300 on the back face thereof.

In the body part 100, there are arranged electrophoresis power source 10, excitation laser source 40 and fluorescence detector unit (for example, CCD camera) 44 and the like.

In the gel electrophoresis part 200, there are arranged a gel plate comprising gel 1 and glass plates 2,3 in a form of cramping the gel, and gel temperature control jackets 131, 132 in a form of cramping the gel plate from both sides thereof, and the like. On the upper end part of the gel plate are arranged a sample placing part and upper buffer solution tank 6; on the lower end part thereof is arranged lower buffer solution tank 5.

In the control unit part 300 are arranged calculation, signal processing and control unit 45, recording and output unit 46, liquid circulating unit with temperature control unit 50 and dry air source 136 and the like.

Firstly, the essential structure for carrying out electrophoresis will be described. Gel 1 is placed between the glass plate 2 and the notched glass plate 3, to compose the gel plate. The method for preparing a gel plate, comprises pouring a non-gelatinized material into the space with spacers 35, 35 interposed between the glass plates 2,3, and composing the gel upper face throughout the entire regions from the left end to the right end in parallel to the lower end face, by using a spacer of a width corresponding to the distance from the left spacer to the right spacer, as a spacer for the gel upper end face, so as to form the gel end face in which shirk comb 61 is inserted. After gel formation, the spacer for the upper end face is removed, and then, by using shirk comb 61 corresponding to the notch width of the gel upper end face, the upper buffer solution covers the whole upper gel end face so that an electric field can be applied vertically at high precision during electrophoresis. Thus, the electric field applied to the gel is not distorted even in a high electric field, to enable stable electrophoresis. As the spacer 35 (spacer on the left side of FIG. 12) on the laser beam-incident face, use was made of an acrylic resin material with certified flatness and transparency of the incident end face.

In the present example, the glass plates 2,3 of a 20-cm square were used as standards, and the size of the gel prepared from the plates was 19 cm (width)×15 cm (length)× 0.35 mm (thickness). But these sizes of the glass plates and gel are only illustrated representatively. These sizes should be changed appropriately, depending on the analytical method, the gel material, and the type of a biological sample to be separated. Because the gel thickness is highly responsible for the generation of Joule's heat as a significant issue of the present invention, these sizes should be determined particularly carefully. Depending on a variety of purposes of analysis, the thickness should be selected, and therefore, the thickness cannot be defined generally. The thickness of for example polyacrylamide gel should be within a practical range of 0.1 to 0.4 mm.

The material of the glass plates 2,3 should have properties to confer surface flatness and higher thermal conductivity together with the properties to attain uniform thickness; and additionally, the material should have good optical transmission with no fluorescent substance contained therein, from the respect of automatic detection via fluorescent labeling. Hence, quartz glass is preferably used as such material. Additionally, the thickness of the glass plates is preferably thin, but the glass plates have to serve for the purpose of flatly holding the gel, and therefore, the plates should be of a thickness with no distortion under the weight of itself. In the present example, non-fluorescent quartz glass of a thickness of 5 mm was used.

For forming sample groove 4, generally, use was made of shirk comb 61 concurrently used. Through the contact of the shirk comb 61 with the gel 1, a plurality of sample grooves 4, 4, - - - are formed. Then, individual samples are filled in the individual sample grooves 4,4, - - - . More specifically, a plurality of biological samples are separately retained in the individual plural grooves formed on the gel upper end face, and these samples are separable under the same conditions during electrophoresis.

In the present example, the pitch of the sample grooves formed by the shirk comb 61 may be determined freely, depending on the sample number to be analyzed simultaneously. A greater number of samples can be analyzed simultaneously at a smaller pitch. As will be described hereinafter, in the present example, the optical system is configured to count samples simultaneously on a vertical line to the electrophoretic direction, so at some pitch, the sensitivity will never severely be reduced. For simultaneously introducing a great number of samples onto a gel, like single electrophoretic analysis of samples simultaneously prepared in a microtiter plate, a multi-head divider at a head pitch corresponding to the pitch of the sample well of the microtiter plate should be used. Then, using a shirk comb at a pitch 1/n ("n" is an integer) -fold the pitch between the heads of the multi-head divider, a plurality of the prepared samples can be introduced into the gel sample grooves at higher efficiency. For example, if a 8-series divider with a pitch of 9 mm is used for a 96-well microtiter plate (12×8) with a well pitch of 9 mm, samples of one row can be transferred at one time. If the pitch of the shirk comb 61 is defined as 1.5 mm (n=6), eight samples in total are introduced every five sample grooves at single dividing procedure; then, the same dividing procedure is repeated after sifting the sample grooves by one by one. Six sets of the dividing procedures can introduce the samples continuously into the 48 sample grooves. If two sets of the above procedures are repeated, 12 sets of dividing procedures in total can introduce the samples in all of the 96 sample grooves. Then, the distance from the right end to the left end of the sample grooves is about 15 cm.

Description will now be made as to how electrophoresis is carried out. At a state of the gel plate prepared as described above and placed in the placing part 200 (the placing method is described hereinafter), the gel plate is arranged at a state cramped between the gel temperature control jackets 131, 132 from both sides thereof; as described below, a coolant transferred out of the liquid circulating unit with temperature control unit 50 and adjusted to an appropriate temperature circulates through tube 29 in the temperature control jackets 131, 132, to control the temperature of the gel plate. As shown in dotted line 47, the laser beam from excitation laser source is incident in parallel to the lower end face of the gel plate through collimating lens 41 and mirror 421 onto a predetermined position in proximity to the lower end part of the gel plate, and the fluorescence from a sample excited via the laser beam is transmitted through slit 134 on the jacket 132 at the position corresponding to the laser beam incident position, and is detected through mirror 422 and polar screen 43 by fluorescence detection unit 44.

The upper end face and lower end face of the gel 1 are immersed in buffer solutions 5 reserved in upper buffer solution tank 6 and lower buffer solution tank 7, respectively. Notched end face of the notched glass plate 3 is beveled, which helps top parts of syringes and the like readily inserted into the sample grooves when the samples are to be introduced therein. Furthermore, the upper buffer solution tank 6 is fixed with clip (not shown in the figures) or the like onto the external face of the notched glass plate 3, and a notch of the same shape as the notch of the glass plate is arranged on the upper buffer solution tank 6 and additionally, sealing material 8, preferably silicon sponge, is arranged following the shape of the notch, to compose a structure such that the leakage of the buffer solution 5 never occurs from the upper buffer solution tank 6. Platinum wire 34 is fixed in each of the upper and lower buffer solution tanks, and one end thereof is connected to banana-clip-type plug 91 or 92, and the plugs 91, 92 are individually connected to power source cable 11 connected to electrophoretic power source 10.

Then, detailed description will now be made of the temperature control means of the gel plate during electrophoresis in the present example. On both sides of the gel plate are pressed and attached, via press plate 19, a pair of jackets 132, 131 with duct line 12 arranged therein. As the material of the jackets 131, 132, aluminum casting (surface treated with alumite) is used, and therefore, these jackets have good thermal conductivity. The jackets are attached closely through highly heat-conductive silicon rubber 133 of a 0.3-mm thickness (see FIG. 16) to the glass faces, so as to maintain face contact thereof and never deteriorate the heat conduction. It is required that the press plate 19 can be removed when the gel plate is inserted or removed at the preparation and completion stages of electrophoresis; and that during electrophoresis, the press plate 19 can keep the gel plate and the jackets 131, 132 attached closely together at the position shown in FIG. 11, so a hinge structure and a cramp mechanism for the press plate 19 should be placed between box 31 of the body part 100 and the press plate 19. For simplification, however, the cramp mechanism is not shown in the figure. The jackets 131, 132 are essentially of the same structure, but the jacket 132 covers a wider area than the whole gel area, while the jacket 131 covers a narrower area by the top end surface of the gel than the whole gel area. This is because of the structural reason such that the end face of the gel 1 can be observed from the side of the jacket 131 even when the bottom positions of the jackets 131, 132 are arranged on the same plane, whereby the introduction of a sample into a well groove or shirk hole can readily be done and the whole system can be maintained at about the objective temperature, immediately after the sample introduction from the jacket 132. Duct line 12 is arranged in a snaking fashion over the whole face of each of the jackets 131, 132. On both the ends of the individual duct lines are arranged individually joints 15, 15 and the duct line on the lower back face of the jacket 132 is connected through the joint 15 to liquid circulating unit 50, for a coolant to be circulated from the unit into the duct line. The duct line on the upper side face of the jacket 132 is connected through the joint 15 to the duct line on the lower side face of the jacket 131, to transfer the coolant passing through the duct line 12 of the jacket 132 into the duct line 12 of the jacket 131. The coolant passing through the duct line 12 of the jacket 132 is circulated back into the liquid circulating unit 50, where the coolant is controlled to a predetermined temperature and again recycled to the duct line of the jacket 132.

The cross section of the duct line 12 is rectangle, which is of a width of 10 mm and a depth of 6 mm in the jacket 132 or which is of a width of 8 mm and a depth of 6 mm in the jacket 131. The thickness of the aluminium plate present between the duct line 12 and the glass 3 is 1 mm. Like the silicon rubber 133, the aluminium plate should have a heat resistance as low as possible. Alternatively, the thickness of the aluminium plate present between the duct line 12 and atmospheric air has a relatively large thermal resistance. Furthermore, the aluminium plate is surrounded by a material with a larger heat resistance, for example bakelite of a thickness of 2 mm. The cross-sectional area of the plate duct line 12 is a determinant of the liquid flow therein, and so as to increase the heat conductivity at a higher flow, the cross-sectional area of the duct line 12 should be designed smaller.

On the front side of the jacket 131, six springs 141, 141, - - - are arranged between the press plate 19 and the jacket 131, and when the press plate 19 is fixed at a predetermined position for electrophoresis, the jacket 131 is pushed against the gel plate. The gel plate is put at a state such that the gel is cramped from both sides thereof with holders 24, 24, - - - fixed on the box 31 of the body part 100, and both the ends of the lower end part are supported by means of supporting block 38. The pressure via the springs 141, 141, - - - structurally works to closely attach together the jacket 131, the gel plate and the jacket 132, to effectively realize heat conduction via the face contact. One end of the press plate 19 is supported by means of the hinge structure 143 fixed on the box 31 of the body part 100, so the press plate can be rotated around the end functioning as the supporting point. For removing the gel plate, the cramp not shown in the figure should be removed, and by subsequently pulling handle 142, the press plate 19 and the jacket 131 are integrally opened. By preparing several types of the jacket 131 and the press plate 19 so as to meet gel plates with different electrophoretic pass lengths. Use of the gel plate with shorter electrophoresis distance results in shorter electrophoretic time.

As shown in FIG. 13, detecting slit 134 is arranged at a position 12 mm above the gel lower end face on the jacket 132. From the side face at the position of the slit 134, laser beam irradiates the gel 1, whereby the fluorescence corresponding to the laser beam excitation and being emitted from a sample on the gel 1 during electrophoresis can be detected through the slit 134. In the present example, the width of the slit 134 is 5 mm, and the temperature control variation on the gel face due to the presence of the slit is at maximum about 10% of the temperature difference between the gel and the jacket. A narrower slit width can effect more precisely such temperature control, but if the width is too narrow, it prevents detection. Hence, the width is defined as 5 mm. The inner wall of the slit 134 and the external jacket 131 corresponding to the position thereof should be colored black, to structurally prevent the occurrence of irregular fluorescent reflection.

Additionally, the jacket 131 has the same duct line cross section and wall thickness as those of the jacket 132, but the jacket 131 has no slit.

As shown in FIGS. 11 and 12, tube 29 is connected to joint 15 in a part of the electrophoresis unit thus structured, and when liquid circulating unit with temperature control unit 50 is connected to the tube 29, then, circulating water or another coolant adjusted to an appropriate temperature can flow in the electrophoresis part. Because the channel formed in the jacket is of a snaking form, and the temperature of gel plate is controlled from both sides thereof, an effective temperature control can be realized at the high heat exchange efficiency. As shown in the arrow in FIG. 11, the flow direction of the coolant into the formed duct line 12 is as follows; the coolant flows starting the bottom part of the jacket 132 on the back face and flows through the duct line 12 out of the joint 15 in the upper part of the jacket 132, and then, the coolant flows in the bottom part of the jacket 131 on the front face and flows through the duct line 12 out of the upper part of the jacket 131, and then returns into the liquid circulating unit with temperature control unit. As has been described above, the liquid flow starts in the bottom part of the jackets, so the air inside the duct line 12 at the initial stage can be purged, to attains stable liquid flow. The material of the tube 29 is preferably silicon rubber protected with an insulating material.

In FIG. 11, "31" is rectangle box and supporting table of the shape of character L. On the vertical face of the character L are arranged slit-equipped temperature control jacket 132 and holder 24; while on the horizontal face of the character L is arranged guide 33 so as to mount the lower buffer solution tank 7 at a predetermined position. A gel plate is positioned and arranged on the supporting table 31 as has been described above, and then, the plate is fixed by means of the press plate, the cramp 14 and the jacket 131. By thereafter covering the plate with lid part 60, dark chamber comprising the lid part 60 and the box and supporting table 31 can be configured.

So as to prevent the occurrence of mildew on the slit part 134 and the signal-transmitting glass plate 2 in contact to the jacket 132, in the electrophoresis system thus arranged, the calculation, signal processing and control unit 45 orders to supply and spray dry air reserved in dry air tank 136, through dry air supply pulp 135, mainly over the detection slit 134, when the jacket temperature is lowered below room temperature.

Then, control and counting will be described below. Electrophoresis power source 10 and liquid circulating unit with temperature control unit 50 are controlled by means of the calculation, signal processing and control unit 45. At the maximum output voltage of 5 kV, the maximum output current of 500 mA and the maximum output power of 500 W, electrophoresis power source 10 can effect feedback control of a constant voltage, a constant current and a constant power. The liquid circulating unit with temperature control unit 50 can control the temperature of the coolant to be circulated into the jackets 131 and 132. The liquid circulating unit with temperature control unit 50 performs temperature control at a liquid flow of 10 liters/min within a temperature range of −30° C. to 90° C. and at a precision of ±0.1° C. The calculation, signal processing and control unit 45 after input with these objective levels can effect individual controls based on the results according to the calculation formulas 1 and 2 with given parameters.

Temperature control will now be described below. Prior to filling the prepared sample into the gel grooves, electric current should be passed through preliminarily (preliminary electrophoresis). In order that the gel temperature might be the objective temperature even during such preliminary electrophoresis, the temperature of the coolant passing through the inside of the jacket should be controlled; additionally, at a voltage applied state of 120 V/cm, the preliminary electrophoresis is to be terminated when the current change per minute reaches below a predetermined current (0.5 mA in the present example). For example, a simple method therefor in some case is to set the duration of electrophoresis for example for 30 minutes. At an high electric field applied, also, if the same level of electric field as the level in actual electrophoresis is applied at the initial stage of preliminary electrophoresis, an excessive initial current (namely excess power) may pass through, depending on the properties of the gel carrier. This causes excess loads to the electric power source and gel deterioration, so the applied voltage at a high electric field applied should be increased gradually over two to three steps.

Detection mechanism will now be described. In FIG. 11, the detection mechanism comprises laser beam source 40 emitting a laser beam at a specific wave length, collimating lens 41 for collimating the laser beam, mirrors 421, 422, polar screen 43 and CCD camera 44. Additionally as the analysis systems, there are arranged computer and memory unit 45 for incorporating the electric signal generated in the CCD camera 44, and the output unit 46, to convert the resulting electric signal into numerical data or image date for analyzing the electrophoresis. Sample to be subjected to the unit should be preliminarily labeled with fluorescence, and therefore, a label appropriate for the excitation beam should be selected. For example, fluorescein isothianate (FITC) is the most appropriate for argon laser, while texas red is suitable for helium-neon laser.

So as to reduce the background during detection, the above structure is placed in a dark chamber comprising the supporting table 31 and the lid part 60. At a predetermined electrophoretic voltage for an electrophoretic duration, electrophoresis is then carried out by presetting the temperature of the water flow to the gel temperature appropriate for good separation during electrophoresis, the sample filled in the gel groove is moved at a strictly temperature controlled state in the gel region (separation zone), until the sample reaches the excitation beam detection zone with a detection window arranged. In the detector 44, the fluorescence is received and detected, through slit 134 structured in the jacket 132, and the detected signals are incorporated sequentially over time into the calculation, signal processing and control unit 45, where the signals are converted into image data and numerical data. Because the fluorescence is incorporated in the increasing order of mobility, these data can be used as the separation data of the sample. Because the slit width is sufficiently narrow as has been described above, almost no variation of the temperature occurs at the detection part; at a high voltage of 240 V/cm, highly reproducible electrophoretic outcome including SSCP patterns can be recovered. Because detection is done outside the temperature control region in the conventional fluorescent electrophoresis system described in the above EMBODIMENT I, the gel temperature as well as the temperature distribution inside the gel is increased outside the temperature-controlled region. Even such increase of the gel temperature and the temperature distribution inside the gel does not cause serious problem for the analytical method with a larger electrophoresis pattern or under no influence of the temperature distribution inside the gel, like DNA sequencing as described in the above EMBODIMENT I (in the electrophoresis for DNA sequencing, the mobility difference in temperature is about 2%/°C.), but for the analytical methods with electrophoretic patterns very sensitive to temperature, like SSCP, the increase of the gel temperature and the temperature distribution inside the gel affects very severely the analytical results. Such problem is overcome by the present inventors, so even SSCP analysis can be realized at a voltage as high as 240 V/cm. It is needless to say that the upper voltage limit durable for electrophoresis should be determined on the basis of the upper limit of the band width being enlarged due to the voltage during electrophoresis but still holding the separation potency, so the upper voltage limit is not restricted to the level described above.

Using the system, genetic polymorphism was analyzed by fluorescence-labeled SSCP method.

In an example described below, the sample analyzed by the genetic analysis described in the above EMBODIMENT I was again analyzed by using the system of the present invention. Subjective genes are not limited to those described in this example; the system is effectively used for a variety of DNA regions such as DNA polymorphism site and mutation site. To elucidate the personal difference in the sequence of the HLA (human leukocyte antigen)-DQA1, the region is analyzed by the asymmetric PCR-SSCP method in accordance with the present invention.

By a standard procedure, genomic DNA of about 1 $\mu$g was extracted from the whole blood (50 $\mu$l), and using 0.1 $\mu$g of the DNA as a template, a PCR reaction solution was prepared in the same manner as described in Japanese Patent Laid-open No. Hei 07-209292 for PCR. Subsequently, asymmetric PCR was carried out by the same method as described in Japanese Patent Laid-open No. Hei 07-209292, and 2 $\mu$l of the resulting reaction product was mixed with 2 $\mu$l of formamide for electrophoresis. However, a fluorescent label rhodamine X isothianate (XRITC), was used by the method described In Japanese Patent Laid-open No. Hei 07-209292, while texas red at an excitation wave length of 594 nm and a fluorescence wave length of 613 nm, was used as a fluorescent label in the present example.

Description will now be made about separating gel. As to the gel, a 11 w/v % (acrylamide bisacrylamide=99:1) acrylamide solution containing TBE buffer (8.9 mM Tris, pH 8.30, 8.9 mM borate, and 2.5 mM EDTA) was firstly degassed, followed by mixing TEMED (tetramethylethylenediamine) to a final concentration of 0.07% and APS (ammonium persulfate) to a final concentration of 0.06% under agitation with the buffer, and the resulting mixture was then poured and polymerized in a space structured by a pair of glass plates and spacers (19-cm width×15-cm application distance×0.35-mm thickness), prior to insertion of a shirk comb. The aforementioned reagents were all available from Nakarai Tesque Co., Ltd. The glass plates retaining the gel were arranged in the electrophoresis system described above.

Figure 15:
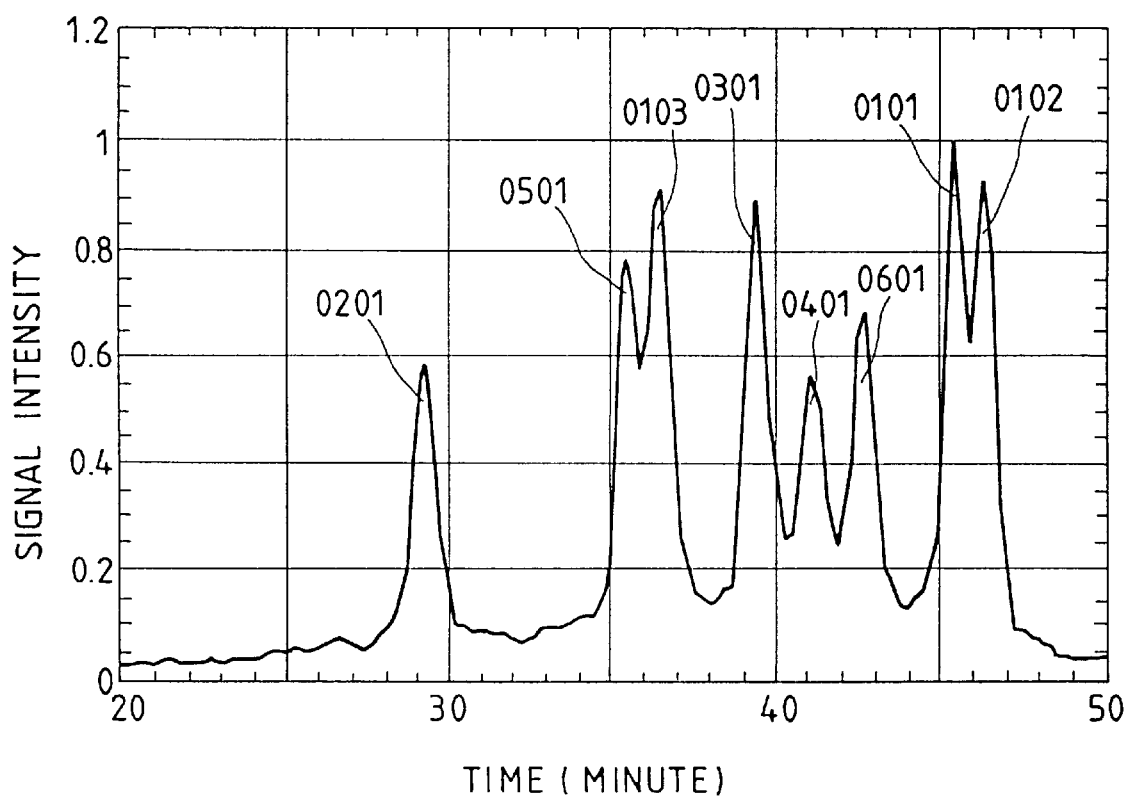
FIG. 15 depicts a view depicting one example of the analysis results in accordance with the present invention.

FIG. 15 is a schematic view depicting the analysis results in accordance with the present invention, wherein data corresponding to one sample groove are shown among all the data. In the sample groove, eight types of samples, namely 0101, 0102, 0103, 0201, 0301, 0401, 0501, and 0601 of the HLA-DQA region, were mixed together and placed. Eight peaks in the figure represent the time required for a single-stranded sense DNA of the HLA-DQA region to be electrophoresed to the detecting position; in other words, the peaks correspond to electrophoretic band patterns. The figure shows that all the eight types of polymorphism were separated. The types of these samples were all preliminarily determined by DNA sequencing, and the individual peaks correspond to the types 0201, 0501, 0103, 0301, 0401, 0601, 0101, and 0102 from left. In the presentexample, 3.6 kV (240 V/cm) was applied, and the analysis of all 30 samples simultaneously electrophoresed was completed in 50 minutes. The power level then applied was 300 W on average, and the temperature of the coolant flowing inside the jacket was −1.6° C.

As in the above EMBODIMENT I, the difference between the gel temperature and the temperature control units (jackets 131, 132) at a predetermined voltage applied and a power level, corresponding to the temperature difference in the coolant, is calculated according to the formula 1, so that the temperature of the coolant should be controlled so as to set the gel temperature at an objective value. If a voltage at a constant power level, namely a constant heat generation, is applied during electrophoresis, the temperature of the coolant is to be constant. Under electrophoretic conditions at a constant voltage applied, the current level is decreased due to the pH change of the buffer at a high voltage, involving the change of the power level; if the temperature of the coolant changes depending on the power level occasionally monitored, however, the gel temperature can be kept constant. Practically, the response of the coolant is about 1° C./min, but the change of the current level (namely the change of power level) is about 0.3 W/min. Therefore, the coolant can be controlled satisfactorily.

Figure 16:
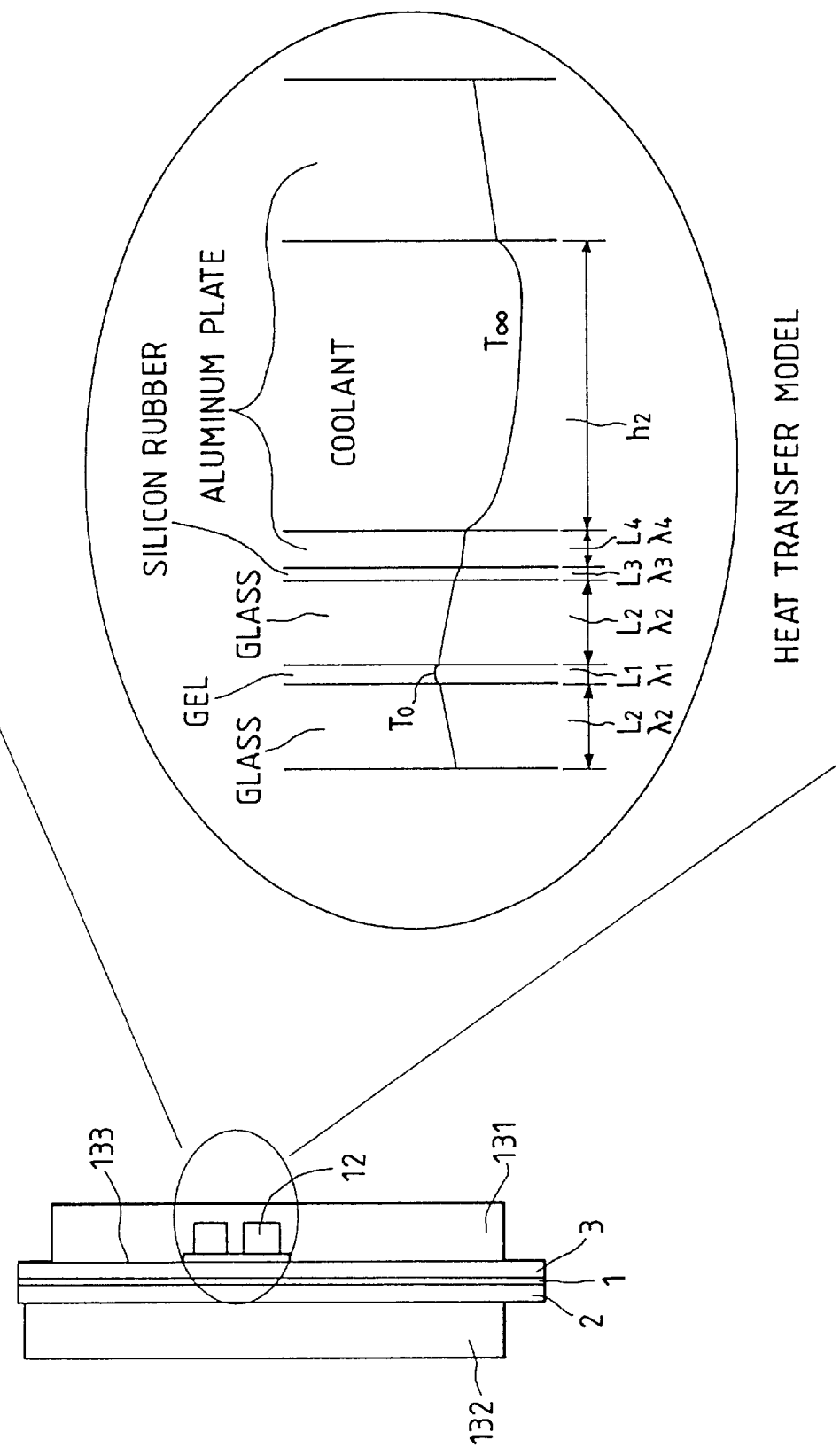
FIG. 16 depicts a typical view of the heat transfer model in accordance with the present invention.

Description will now be made of heat conductive parameters and heat conduction calculation formulas, corresponding to the system structure of the present example. FIG. 16 is a schematic view depicting the temperature control jackets and gel plate of the present system. In the system, the gel is uniformly (equally) temperature controlled from both of the left and right sides of the figure. Thus, as a heat transfer model, a heat transfer model with an heat source in the center should be assumed satisfactory (calculation formula 1). For forced liquid convection at a flow of 10 liters/min circulating, the heat conductivity "h2" is calculated to be 5.4×10 W/m.K. Based on the gel area "A", the heat flux "G/2A" is represented as G(W)×35.1 (m/W) using the applied power level "G(W)" during electrophoresis; providing gel thickness L1=0.35 mm, glass plate thickness L2=5 mm, silicon rubber thickness L3=0.3 mm, aluminum plate thickness L4=1 mm, gel heat conductivity l1=0.59 W/m.K, glass plate heat conductivity l2=1.35 W/m.K, silicon rubber heat conductivity l3=3.8 W/m.K, aluminum plate heat conductivity l4=204 W/m.K along with the value of "h2", the relation between the gel center temperature "T0" and the coolant temperature "T∞" can be represented as a formula (calculation formula 2) with applied power G(W) under various electrophoretic conditions, using the formula 1 in accordance with the present EMBODIMENT II.

$$T_\infty = T_0 - \frac{G}{2A}\left(\frac{L_1}{4\lambda_1} + \frac{L_2}{\lambda_2} + \frac{L_3}{\lambda_4} + \frac{1}{h_2}\right) \quad \text{(formula 1)}$$

$$T_\infty = T_0 - 0.0072G \quad \text{(formula 2)}$$

In the present example, if the temperatures of the jackets 131, 132 during electrophoresis are far lower than room temperature, which disadvantageously causes the occurrence of mildew on the external surface of the jackets, the lid part 60 of the placing part 200 in the gel electrophoresing part should be arranged with a low-temperature control function to generate preferentially mildew on the lid part 60, along with duct line 62 to discharge water droplet, whereby the occurrence of mildew on the jackets should preferably be prevented. More specifically, the lid part 60 should be made of a material with good heat transfer properties, and a Peltier element is attached onto the inside thereof, and then, setting the side of the lid part 60 at high temperatures, the side of the placing part 200 can be set at lower temperatures, where the Peltier element can induce mildew, whereby the occurrence of mildew can be prevented on the jackets.

In the present example, furthermore, the fluorescence detector is of a surface detection type (CCD) capable of detecting signal light transmitted through the slit 134, but it is needless to say that the detector may satisfactorily be of a type such that a laser beam source and a detector are integrated together to irradiate an excitation beam and detect signal light at the mechanically scanned position of a slit.

An another example will be described where the system Is used as a DNA sequencer for DNA sequencing. The template and reagents contained in a sequencing kit (Code M13-110; manufactured by Toyobo Co., Ltd.) including an enzyme produced by modified T7 polymerase, were used; following the protocol as described in the attached instruction leaflet, reaction was effected. By filling the resulting reaction solution in sample groove 4, followed by application of an electrophoresis voltage of 160 V/cm to preset the gel temperature at 55° C., separation was progressed. The gel composition was prepared as follows; Longranger as a trade name (manufactured by FMC) at 6% concentration was polymerized according to a standard protocol. The denaturing agent was urea at a concentration of 7 M. The analysis of a sample with a DNA fragment with 400 bases was completed in 30 minutes, to generate good nucleotide sequence data. As to the electrophoretic conditions, the time required for the electrophoresis is about 1/10 fold the separation time required for conventional DNA sequencing, which indicates that very rapid separation can be carried out under the present conditions. A short fragment such as PCR product can be analyzed in a short time because the electrophoresis thereof takes as short a time as about 30 minutes, and therefore, after the completion of first electrophoresis, intermediate electrophoresis should be carried out for discharging the remaining sample for about 10 minutes. In such case, a fresh sample can be introduced again for DNA sequencing. In such manner, DNA sequencing can be repeated. In the present example, fragments of about 400 bases could be continuously analyzed three to four times, depending on the fragment length to be analyzed. This may possibly be due to the advantage of the present invention, such that precise temperature control can cause extremely lesser deterioration of the gel.

As shown in the above two examples, in accordance with the present invention, both of the simple fragment analysis represented by SSCP and RFLP, and detailed sequence analysis by DNA sequencing can be carried out very speedily, by using two substantially same analyzer mentioned above sequentially, where a appropriate gel for each analyzer is chosen. By this method, processes from the screening to detailed sequence analysis of a mutant gene can be configured as a sequential system.

Figure 17:
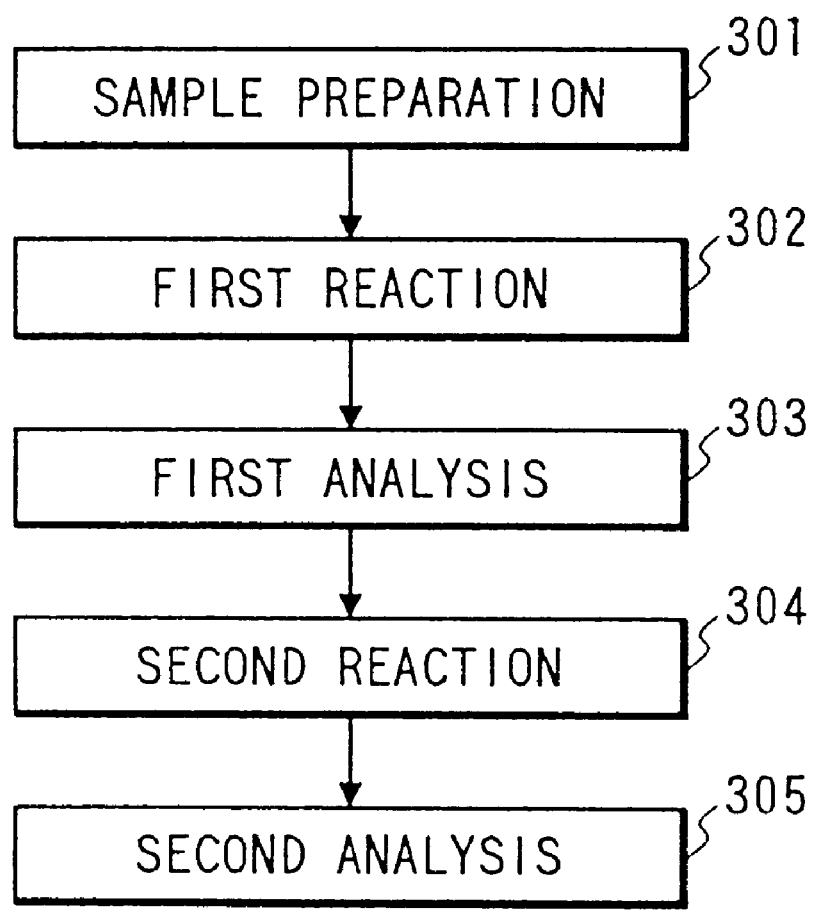
FIG. 17 is a flowchart depicting an example, wherein a series of procedures are practiced in a flow from screening to detailed sequence analysis.

FIG. 17 is a flowchart depicting an example realizing the screening to detailed sequence analysis by a series of procedures.

As shown in the figure, a sample containing at least one target gene is prepared (301). Then, a first reaction process for selectively amplifying the target gene is done (302). More specifically, for example, the process is PCR. Subsequently, a part of a sample produced by amplifying a preliminarily selected region, namely a part of the PCR product, is subjected to screening by a simple fragment analysis, for example, SSCP, by using the DNA analyzer of the present example, to identify a reaction product with a signal different from normal one or a reaction product specified by the operator (303). Among the reaction products of the first reaction, only the specified sample is subjected to a second reaction process as the pretreatment for DNA sequencing (304). This process corresponds to a process of carrying out the sequencing reaction by the Sanger method. Subsequently, a part of the second reaction product is sequenced by the DNA analyzer of the example (305). In this case, the screening as step 303 and the sequencing as step 305 are the same in terms of the apparatus structure used and the procedures using the apparatus, except for the gel composition for separation and separation conditions (temperature and electric field intensity). Thus, an operator should charge preliminarily prepared individual gel carriers in each of two sets of such DNA analyzer, to effect the first reaction process for screening on the first DNA analyzer and to effect the second reaction process for serial DNA sequencing on the second DNA analyzer, using the results generated above. In accordance with the present invention, accordingly, preliminary electrophoresis for about 10 minutes after first electrophoresis as described above can directly be proceeded to next electrophoresis with no gel change. While DNA sequencing is carried out on the second DNA analyzer, therefore, a first reaction process of next group of samples and the screening procedure thereof on the first DNA analyzer can be carried out satisfactorily.

As the first and second reaction systems, use may be made of the same reaction system as disclosed in Japanese Patent Laid-open No. Hei 6-327476.

The serial screening and DNA sequencing processes are illustrated in an example of the mutation analysis of a tumor suppresser gene p53. In the present example, the subject was genomic DNA; eight regions of the p53 gene, namely exon 4 (320), 5 (222), 6(149), 7 (153), 8 (170), 9 (104), 10 (142), and 11 (133), were analyzed (In parenthesis, the nucleotide length of each amplified product is shown). As the PCR primer sequence and PCR conditions, those described in Oncogene, 7, pp. 451–457, 1992 by Sameshima et. al. were selected. Firstly, DNAs are extracted from a subjective sample and control (normal sample) by a standard procedure, and a region to be analyzed should be PCR amplified on the first reaction system. In the present example, 48 samples were amplified from each exon. Subsequently, a part (10%) of the amplification product is introduced in the DNA analyzer to carry out screening of the mutant gene by the SSCP method. Using the gel of the same composition as shown in Example 1, electrophoretic separation was carried out at a gel temperature of 20° C. and an electric field intensity of 160 V/cm. In about 60-minute electrophoresis, all the samples were separated. Displaying the signals from the separated electrophoretic pattern on the signal processing means, a sample observed to have a pattern different from normal one should be identified. Then, only the designated sample is transferred to the second reaction system, where purification and sequencing thereof are carried out. Among the 48 samples simultaneously analyzed, up to 8 of the samples were observed with variation of the patterns after the screening. More specifically, the efficiency was improved by about 5-fold or more by such screening. Generally, one gene is composed of a plurality of exon regions, so such high level of the efficiency can be expected naturally. The purification was carried out by standard procedures, including ethanol precipitation; the sequencing was carried out through direct sequencing by the Sanger method using a primer label of a single color (texas red).

As has been described above, the samples prepared on the second reaction system are placed in the DNA analyzer placing therein the gel of the composition shown in second Example for DNA sequencing. In the present example, the electric field intensity was 120 V/cm, but any of the samples could be electrophoresed within 30 minutes because the subjective fragment length was short.

Because sequencing was effected by means of single-color primer label in the present example, the DNA sequences of only 12 samples could be simultaneously determined in 48 lanes. Since the analyzing subjects were restricted to 4 to 8 samples via the screening, however, the processing ability thereof was satisfactory. In other words, the present system can carry out all the processes of mutation analysis in a sequentially, because the sequencing reaction process and DNA sequencing process do not work any more as rate-determining steps therein since sample number for second analysis is reduced by screening done by first analysis. Additionally, in accordance with the present invention, high-speed screening and high-speed DNA sequencing are attained so that the process from screening to DNA sequencing of 48 samples could be completed in about 5 hours. The processing time was assigned as follows; 1.5 hours on the first reaction unit; one hour for SSCP analysis on the DNA analyzer; 2 hours on the second reaction unit; and 30 minutes for DNA sequencing on the DNA analyzer. The time required for screening and the time required for DNA sequencing are equally 2.5 hours. When, as described above, two sets of the DNA analyzer of the present invention are independently used for screening and DNA sequencing, the procedures therefore can progress in sequentially. In this case, it is estimated that 384 samples in total (48 samples×8 exon regions) can be analyzed in about 23 hours. When the same volume of samples is to be analyzed wholly by DNA sequencing, alternatively, about 12 hours are required per 48 samples; additionally, continous processing is hard to practice because the second reaction process and DNA sequencing process work as rate-determining steps. Thus, 384 samples in total require approximately 96 hours. When all the samples are to be analyzed by DNA sequencing, furthermore, a vast number of normal samples have to be analyzed simultaneously, to provide only useless sequence data at higher reagent cost.

In accordance with the present EMBODIMENT II, the gel including a part irradiated with an excitation beam during electrophoresis can be temperature controlled overall at a higher efficiency, and even at a higher voltage applied, a highly reproducible and markedly separated electrophoretic pattern by SSCP analysis or DNA sequencing can be generated. All the processes from the screening to DNA sequencing of a mutant gene can be practiced speedily and highly efficiently.

We claim:

1. A DNA analyzer comprising an automatically detecting gel electrophoresis system, comprising;

a gel electrophoresis part including a gel for gel electrophoresis of a substance with a fluorescent activity and translucent plates supporting the gel between the plates;

a pair of temperature control units arranged on both outer faces of the supporting plates, respectively, and covering a full area for gel electrophoresis operation, wherein each temperature control unit has a duct line arranged in a snaking fashion and through which a coolant flows in order to remove heat generated in the gel and one of the temperature control units has a light-transmitting slit at a lower part thereof and at a part which is not the duct line;

temperature regulating elements regulating coolant temperature;

upper and lower buffer solution tanks in contact with the gel and the supporting plates;

electrodes immersed in the buffer solutions in the solution tanks;

a power source element applying a predetermined electric field for gel electrophoresis operation through the electrodes to the gel;

an optical element irradiating a predetermined excitation beam over the gel and an optical element receiving the signal light from the gel, wherein at least one of irradiation of the excitation beam over the gel, or detection of the signal light from the gel, can be carried out through the slit; and a signal processing element memorizing and processing the signal light data received, wherein said temperature regulating elements control the coolant temperature based on predetermined formulas with measured input power and given parameters of said temperature control units and gel plates, so as to make substantially equal the power input to the gel by said power source element, and the power removed by the coolant, depending on the temperature gradient of the gel temperature and the coolant temperature.

2. A DNA analyzer according to claim 1, wherein the sample-introducing end face of the gel is configured in the gel electrophoresis system so that the end face might be parallel to the lower end face from the left to right ends of the gel.

3. A DNA analyzer according to claim 1, wherein the temperature control units arranged on both sides of the gel are of a size such that one of the elements might cover the sample-introducing position and the other of the elements might not cover the sample introduction position but be arranged so as to visually observe a sample to be introduced therein.

4. A DNA analyzer according to claim 1, wherein the slit part is provided with a blowout hole of dry air or air above the temperature of the temperature control units.

5. A DNA analyzer according to claim 1, wherein said gel electrophoresis part further comprises a cooling plate for controlling temperatures below the temperature of the temperature control units, and a duct line for collecting and transferring water droplets mildewed on the cooling plate.

6. A DNA analyzer according to claim 1, wherein said power source element applies more than 80 V/cm electric field for gel electrophoresis operation through the electrodes to the gel.

7. A DNA analyzer according to claim 1, wherein said power source element applies more than 30w of power for gel electrophoresis operation through the electrodes to the gel.

8. A DNA analyzer system, comprising;
an automatically detecting gel electrophoresis system comprising a gel for gel electrophoresis of a substance with a fluorescent activity and translucent supporting plates supporting the gel between the plates:
a pair of temperature control units arranged on both outer faces of the supporting plates respectively and covering a full area for gel electrophoresis operation, wherein each temperature control unit has a duct line arranged in a snaking fashion and through which a coolant flows in order to remove heat generated in the gel and one of the temperature control units has a light-transmitting slit at a lower part thereof and at a part which is not the duct line;
temperature regulating elements regulating the coolant temperature;
upper and lower buffer solution tanks in contact with the gel and the supporting plates;
electrodes immersed in the buffer solutions in the solution tanks;
a power source element applying a predetermined electric field for gel electrophoresis operation through the electrodes to the gel; and
an optical element irradiating a predetermined excitation beam over the gel and,
an optical element receiving the signal light from the gel, wherein at least one of irradiation of the excitation beam over the gel or detection of the signal light from the gel can be carried out through the slit; and
a signal processing element memorizing and processing the signal light data received,
wherein said light-transmitting slit is arranged in a surface of at least one of a pair of said temperature control units, which surface is over a face of the gel and within a region the duct line circumscribes, and
wherein said temperature regulating elements control the coolant temperature so as to maintain substantially equal power input to the gel by said power source element and a calculated power as input to the gel based on predetermined formulas with given parameters of said temperature control units and a measured temperature of a plate face in contact with the coolant, and
whereby the gel during electrophoresis and detection can be temperature controlled;
a first reaction unit for selectively amplifying and labeling at least one target DNA;
a second reaction unit for carrying out a preliminary process for DNA sequencing;
a transfer means for transferring a part of the reaction product in the first reaction unit to a sample introducing groove positioned on the upper part of the gel in the DNA analyzer;
a transfer means for transferring the reaction solution from at least one of the reaction vessels in the first reaction unit to the second reaction unit;
a transfer means for transferring a part of the reaction product in the second reaction unit to a sample-introducing groove positioned on the upper part of the gel in the DNA analyzer;
at least one regulation means for regulating the first and second reaction units and transfer means; and,
a signal processing means for memorizing and displaying signals in the DNA analyzer,
wherein a predetermined region of a sample is selectively amplified in the first reaction unit and a part of the reaction product is screened by simple fragment analysis for example SSCP using the DNA analyzer, to transfer a reaction product with abnormal signals or a reaction product designated by an operator to the second reaction unit, where the reaction product is preliminarily treated for DNA sequencing and the resulting product after the preliminary treatment is again introduced in the DNA analyzer where the nucleotide sequence of the product is determined.

9. A DNA analyzer according to claim 8, wherein said power source element applies more than 80 V/cm electric field for gel electrophoresis operation through the electrodes to the gel.

10. A DNA analyzer according to claim 8, wherein said power source element applies more than 30w of power for gel electrophoresis operation through the electrodes to the gel.

11. A DNA analyzer comprising an automatically detecting gel electrophoresis system, comprising;
a gel for gel electrophoresis of a substance with a fluorescent activity and translucent plates supporting the gel;
a pair of temperature control units arranged on both outer faces of the plates and a pair of temperature regulating elements regulating the temperature control units;
upper and lower buffer solution tanks for supplying buffer solutions in contact with the gel and the plates;
electrodes immersed in the buffer solutions in the solution tanks;
a power source element applying a predetermined electric field through the electrodes to the gel;
an optical element irradiating a predetermined excitation beam over the gel, and an optical element receiving the signal light from the gel; and,
a signal processing element memorizing and processing the signal light data received, wherein a light-transmitting slit is arranged on at least one of the pair of the temperature control units, and through the slit, at least one of irradiation of the excitation beam over the gel or detection of the signal light from the gel can be carried out, wherein said light-transmitting slit is arranged in a surface of at least one of a pair of said temperature control units, which surface is over a face of the gel and within a region the duct line circumscribes, and wherein the slit part is provided with a blowout hole of air above the temperature of the temperature control units.

12. A DNA analyzer comprising an automatically detecting gel electrophoresis system, comprising;

a gel electrophoresis part including a gel for gel electrophoresis of a substance with a fluorescent activity and translucent plates supporting the gel between the plates;

a pair of temperature control units arranged on both outer faces of the plates respectively and covering a full area for gel electrophoresis operation, wherein each temperature control unit has a duct line arranged in a snaking fashion and through which a coolant flows in order to remove heat generated in the gel and one of the temperature control units has a light transmitting slit at a lower part thereof which is not the duct line; and wherein said light transmitting slit is arranged in a surface of at least one of a pair of said temperature control units, and wherein said surface is over a face of the gel and within a region the duct line circumscribes, temperature regulating elements regulating coolant temperature;

upper and lower buffer solution tanks in contact with the gel and the supporting plates;

electrodes immersed in buffer solutions in the solution tanks;

a power source element applying a predetermined electric field for gel electrophoresis operation through the electrodes to the gel;

an optical element irradiating a predetermined excitation beam over the gel, and an optical element receiving the signal light from the gel, wherein at least one of irradiation of the excitation beam over the gel, or detection of the signal light from the gel, can be carried out through the slit; and, a signal processing element memorizing and processing the signal light data received, wherein the coolant temperature is controlled to be maintained to a predetermined set value.

13. A DNA analyzer comprising an automatically detecting gel electrophoresis system, comprising;

a gel electrophoresis part including a gel for gel electrophoresis of a substance with a fluorescent activity and translucent plates supporting the gel between the plates;

a pair of temperature control units arranged on both outer faces of the supporting plates, respectively and covering a full area for gel electrophoresis operation, wherein each temperature control unit has a duct line arranged in a snaking fashion and through which a coolant flows in order to remove heat generated in the gel and one of the temperature control units has a light transmitting slit at a lower part thereof and at a part which is not the duct line; and wherein the light transmitting slit is arranged on a surface of at least one of a pair of temperature control units, and wherein said surface is over a face of the gel and within a region the duct line circumscribes, temperature regulating elements regulating coolant temperature;

upper and lower buffer solution tanks in contact with the gel and the supporting plates;

electrodes immersed in buffer solutions in the solution tanks, a power source element applying a predetermined electric field for gel electrophoresis operation through the electrodes to the gel;

an optical element irradiating a predetermined excitation beam over the gel and an optical element receiving the signal light from the gel, wherein at least one of irradiation of the excitation beam over the gel, or detection of the signal light from the gel, can be carried out through the slit; and a signal processing element memorizing and processing the signal light data received, wherein the coolant temperature is controlled to be maintained to a predetermined set value according to a measured initial input power to the gel.

14. A DNA analyzer according to claim 13, wherein said temperature control unit controls gel temperature within a temperature range of −30° C. to 90° C. at a precision of ±0.1° C.

* * * * *